US009186179B2

(12) United States Patent
Mullaney

(10) Patent No.: US 9,186,179 B2
(45) Date of Patent: Nov. 17, 2015

(54) REVOLVING LOCK FOR EXTERNAL FIXATION CLAMPS

(75) Inventor: Michael W. Mullaney, Kinnelon, NJ (US)

(73) Assignee: Zimmer, Inc., Warsaw, IN (US)

( * ) Notice: Subject to any disclaimer, the term of this patent is extended or adjusted under 35 U.S.C. 154(b) by 771 days.

(21) Appl. No.: 13/315,574

(22) Filed: Dec. 9, 2011

(65) Prior Publication Data

US 2012/0150185 A1 Jun. 14, 2012

Related U.S. Application Data

(60) Provisional application No. 61/421,502, filed on Dec. 9, 2010.

(51) Int. Cl.
*A61B 17/64* (2006.01)

(52) U.S. Cl.
CPC .................................. *A61B 17/6466* (2013.01)

(58) Field of Classification Search
CPC ... A61B 17/6466; A61B 17/645; A61B 17/60
USPC ............. 403/385, 389, 396, 321, 322.1, 325, 403/326; 606/54, 59
See application file for complete search history.

(56) References Cited

U.S. PATENT DOCUMENTS 1,706,215 A 3/1929 Davidson
2,705,603 A 4/1955 Bitz et al.
3,044,512 A 7/1962 Jones
3,154,331 A 10/1964 Engelhardt
3,373,465 A 3/1968 Johnson et al.
3,406,987 A 10/1968 Hunder et al.
4,037,978 A 7/1977 Connelly
4,115,966 A 9/1978 DeLee
4,312,488 A 1/1982 Pierron
4,379,579 A * 4/1983 Mahan et al. .............. 294/82.36
4,388,747 A 6/1983 Plummer
4,483,334 A 11/1984 Murray (Continued)

FOREIGN PATENT DOCUMENTS

DE 2430234 1/1975
EP 1820461 8/2007

(Continued)

OTHER PUBLICATIONS

International Searching Authority/European Patent Office, "Notification of Transmittal of the International Search Report and the Written Opinion of the International Searching Authority, or the Declaration," for PCT/US2011/963985, mailed Mar. 28, 2012, 10 pages.

(Continued)

*Primary Examiner* — Daniel Wiley
(74) *Attorney, Agent, or Firm* — Schwegman Lundberg & Woessner, P.A.

(57) ABSTRACT

A clamp assembly includes a first jaw and a second jaw cooperatively positioned to receive the fixation element. A gate is displaceable relative to the first jaw and moveable between an open condition where the gate and the first jaw form an opening of a first size allowing introduction of the fixation element between the first and second jaws and a locking condition where the opening formed by the gate and the first jaw has a second size that prevents removal of the fixation element out from between the first and second jaws.

21 Claims, 18 Drawing Sheets

102 112 120 178 168 172 130 130 126 124 152 118 159 142 152 160 156 122 158 140 128 162 160 144 154 156 157 154 158 152 122 134 136 138

(56) References Cited

U.S. PATENT DOCUMENTS

| | | | | |
|---|---|---|---|---|
| 4,620,533 | A | 11/1986 | Mears | |
| 4,653,481 | A | 3/1987 | Howland et al. | |
| 4,662,365 | A | 5/1987 | Gotzen et al. | |
| 4,700,437 | A | 10/1987 | Hoshino | |
| D295,725 | S | 5/1988 | Shioda | |
| 4,817,897 | A | 4/1989 | Kreusel | |
| 5,312,405 | A | 5/1994 | Korotko et al. | |
| 5,427,465 | A | 6/1995 | Sato | |
| 5,662,648 | A | 9/1997 | Faccioli et al. | |
| 5,683,389 | A | 11/1997 | Orsak | |
| 5,709,681 | A | 1/1998 | Pennig | |
| 5,727,899 | A | 3/1998 | Dobrovolny | |
| 5,741,252 | A | 4/1998 | Mazzio et al. | |
| 5,746,741 | A | 5/1998 | Kraus et al. | |
| 5,752,954 | A | 5/1998 | Mata et al. | |
| 5,800,548 | A | 9/1998 | Martin et al. | |
| 5,827,282 | A | 10/1998 | Pennig | |
| 5,860,728 | A | 1/1999 | Maglica | |
| 5,891,144 | A | 4/1999 | Mata et al. | |
| 5,976,141 | A | 11/1999 | Haag et al. | |
| 6,022,348 | A | 2/2000 | Spitzer | |
| 6,080,153 | A | 6/2000 | Mata et al. | |
| 6,102,911 | A | 8/2000 | Faccioli et al. | |
| 6,217,577 | B1 | 4/2001 | Hofmann | |
| 6,277,069 | B1 | 8/2001 | Gray | |
| 6,305,868 | B1 * | 10/2001 | Kinoshita et al. | 403/49 |
| 6,376,775 | B1 | 4/2002 | Leijon et al. | |
| 6,386,786 | B1 | 5/2002 | Perlman et al. | |
| 6,409,729 | B1 | 6/2002 | Martinelli | |
| 6,500,177 | B1 | 12/2002 | Martinelli et al. | |
| 6,637,082 | B1 | 10/2003 | Chang | |
| 6,652,523 | B1 | 11/2003 | Evrard et al. | |
| 6,702,814 | B2 | 3/2004 | Walulik et al. | |
| 6,716,212 | B1 | 4/2004 | Pickens | |
| 6,736,775 | B2 | 5/2004 | Phillips | |
| 7,004,943 | B2 | 2/2006 | Ferrante et al. | |
| 7,048,735 | B2 | 5/2006 | Ferrante et al. | |
| 7,097,616 | B2 * | 8/2006 | Bjork et al. | 600/230 |
| 7,241,071 | B2 | 7/2007 | Carraher et al. | |
| 7,241,074 | B2 | 7/2007 | Thomket et al. | |
| 7,261,713 | B2 | 8/2007 | Langmaid | |
| 7,314,331 | B1 | 1/2008 | Koros et al. | |
| 7,320,556 | B2 | 1/2008 | Vagn-Erik | |
| 7,491,008 | B2 | 2/2009 | Thomke et al. | |
| 7,527,626 | B2 | 5/2009 | Lutz et al. | |
| 7,562,855 | B2 | 7/2009 | Oetlinger | |
| 7,708,736 | B2 | 5/2010 | Mullaney | |
| 7,887,537 | B2 | 2/2011 | Ferrante et al. | |
| 7,938,829 | B2 | 5/2011 | Mullaney | |
| 2001/0004432 | A1 | 6/2001 | Pfister | |
| 2002/0037193 | A1 | 3/2002 | Gibbons et al. | |
| 2002/0042613 | A1 | 4/2002 | Mata | |
| 2002/0061225 | A1 | 5/2002 | Boucher et al. | |
| 2002/0165543 | A1 | 11/2002 | Winquist et al. | |
| 2003/0120132 | A1 | 6/2003 | Phillips | |
| 2003/0149429 | A1 | 8/2003 | Ferranet et al. | |
| 2004/0044344 | A1 | 3/2004 | Winquist et al. | |
| 2005/0113831 | A1 | 5/2005 | Franck et al. | |
| 2006/0039750 | A1 | 2/2006 | Thomke | |
| 2006/0178566 | A1 * | 8/2006 | Fetzer | 600/234 |
| 2006/0229602 | A1 | 10/2006 | Olsen | |
| 2006/0229603 | A1 | 10/2006 | Olsen | |
| 2006/0255521 | A1 | 11/2006 | Brunner | |
| 2006/0271045 | A1 | 11/2006 | Hubbard et al. | |
| 2006/0287652 | A1 | 12/2006 | Lessig et al. | |
| 2007/0038217 | A1 | 2/2007 | Brown et al. | |
| 2007/0049932 | A1 | 3/2007 | Richelsoph et al. | |
| 2007/0055110 | A1 | 3/2007 | Bass | |
| 2007/0198012 | A1 | 8/2007 | Thomke et al. | |
| 2007/0293860 | A1 | 12/2007 | Oesch | |
| 2008/0065068 | A1 | 3/2008 | Thomket et al. | |
| 2008/0177315 | A1 | 7/2008 | Usher | |
| 2008/0215053 | A1 | 9/2008 | Thomke et al. | |
| 2009/0036891 | A1 | 2/2009 | Brown et al. | |
| 2009/0088751 | A1 | 4/2009 | Mullaney | |
| 2009/0299368 | A1 | 12/2009 | Bauer | |
| 2011/0098706 | A1 | 4/2011 | Mullaney | |
| 2011/0098707 | A1 | 4/2011 | Mullaney | |
| 2011/0172663 | A1 | 7/2011 | Mullaney | |
| 2012/0004659 | A1 | 1/2012 | Miller et al. | |
| 2012/0089142 | A1 | 4/2012 | Mullaney et al. | |
| 2012/0095462 | A1 | 4/2012 | Miller | |

FOREIGN PATENT DOCUMENTS

| | | |
|---|---|---|
| EP | 2294994 | 3/2011 |
| WO | WO-89/05126 | 6/1989 |
| WO | WO-90/11055 | 10/1990 |
| WO | WO-92/12683 | 8/1992 |
| WO | WO-98/51227 | 11/1998 |
| WO | WO-99/25264 | 5/1999 |
| WO | WO-03065911 | 8/2003 |
| WO | WO 2009/004347 | 1/2009 |
| WO | WO-2012078897 | 6/2012 |

OTHER PUBLICATIONS

"International Application Serial No. PCT/US2011/063985, International Preliminary Report on Patentability mailed Jun. 20, 2013", 6 pgs.

European Patent Office, International Search Report and Written Opinion mailed Mar. 20, 2012, Application No. PCT/US2011/059303, 13 pages.

European Patent Office, International Search Report and Written Opinion mailed Apr. 10, 2012, Application No. PCT/US2011/063976, 8 pages.

European Patent Office, International Search Report and Written Opinion mailed Jan. 9, 2012, Application No. PCT/US2011/055907, 9 pages.

Swiss Patent Office, Application No. 03 891/90-6, titled "Fixateur externe," Applicant—Jaquet Orthopedie S.A., filed Dec. 16, 1991, 34 pages.

European Patent Office, International Search Report and Written Opinion dated Oct. 13, 2011, Application No. PCT/US2011/042813, 11 pages.

PCT/ISA-US Office, International Search Report and Written Opinion dated Dec. 2, 2008, Application No. PCT/US08/77800, 11 pages.

* cited by examiner

REVOLVING LOCK FOR EXTERNAL FIXATION CLAMPS

PRIORITY

This application claims priority to U.S. Provisional Patent Application 61/421,502, filed Dec. 9, 2010, incorporated herein by reference.

FIELD OF THE INVENTION

This application is directed to an external fixation system, and more particularly, this disclosure is directed to an external fixation clamping assembly having a clamp with a gate element.

BACKGROUND

External fixation systems are used to stabilize fractured bones or secure bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened. Some conventional clamps have to be tightened partially to provisionally lock the bone pin or bar into the clamp. Others require insertion of a fixation element against a spring force possibly making insertion more difficult than necessary.

The present disclosure overcomes one or more of the deficiencies in the prior art.

SUMMARY

In one exemplary aspect, the present disclosure is directed to a clamp assembly configured to secure a fixation element of an external fixation system. The clamp assembly includes a first jaw and a second jaw disposed relative to the first jaw. The first and second jaws are cooperatively positioned to receive the fixation element. The clamp assembly also includes a gate displaceable relative to the first jaw and moveable between an open condition where the gate and the first jaw form an opening of a first size allowing introduction of the fixation element between the first and second jaws and a locking condition where the opening formed by the gate and the first jaw has a second size that prevents removal of the fixation element out from between the first and second jaws.

In one aspect, the clamp assembly also includes a biasing element that is positioned and configured to bias the gate toward the locking condition. In one aspect, the gate is a revolving gate. In yet another aspect, the clamp assembly includes a release mechanism configured to displace the gate to the open condition allowing removal of the fixation element from the clamp. The release mechanism may include a slider actuatable by a user and a gate release portion associated with the slider.

In another exemplary aspect, the present disclosure is directed to a clamp assembly configured to secure a fixation element of an external fixation assembly. The clamp assembly includes a first jaw having a fixation element interfacing surface and a rigid gate supporting portion. The interfacing surface and the gate supporting portion may form an opening sized to receive the fixation element. A gate is supported by the gate supporting portion, with the gate being displaceable relative to the first jaw and moveable between an open condition where the gate is spaced from the first jaw a first distance allowing introduction of the fixation element into the clamp assembly and a locking condition where the gate is spaced from the first jaw a second distance that prevents removal of the fixation element from the clamp assembly.

In one aspect, a second jaw is disposed opposite the first jaw. The second jaw may have a fixation element interfacing surface opposing the fixation element interfacing surface of the first clamp and cooperating with the fixation element interfacing surface of the first jaw to secure the fixation element in a fully locked condition.

In another exemplary aspect, the present disclosure is directed to a clamp assembly that includes a first jaw and a second jaw disposed relative to the first jaw. The first and second jaws may form an opening sized to receive the fixation element. A gate is displaceable relative to the first jaw and displaceable relative to the second jaw in a position controlling access to the opening formed by the first and second jaws. The gate may be moveable between an open condition where the gate permits a fixation element to access the opening formed by the first and second jaws and a locking condition where the gate prevents removal of the fixation element through the opening formed by the first and second jaws.

In another exemplary aspect, the present disclosure is directed to a clamp having an opening structurally arranged to receive a fixation element. The clamp may include a revolving gate disposed relative to an opening in a position controlling access to the opening. The gate may revolve between an open condition where the gate permits a fixation element to pass through the opening and a locking condition where the gate prevents removal of the fixation element through the opening.

In another exemplary aspect, the present disclosure is directed to a method of clamping an external fixation element with an external fixation clamp. The method may include introducing a fixation element into an opening of the clamp, rotating a gate portion to allow the fixation element to enter a seated position in the clamp, and rotating the gate portion to prevent the fixation element from being removed from clamp. In one aspect, the method may include clamping the fixation element between a first jaw and a second jaw.

BRIEF DESCRIPTION OF THE DRAWINGS

Aspects of the present disclosure are best understood from the following detailed description when read with the accompanying figures.

DETAILED DESCRIPTION

Figure 1:
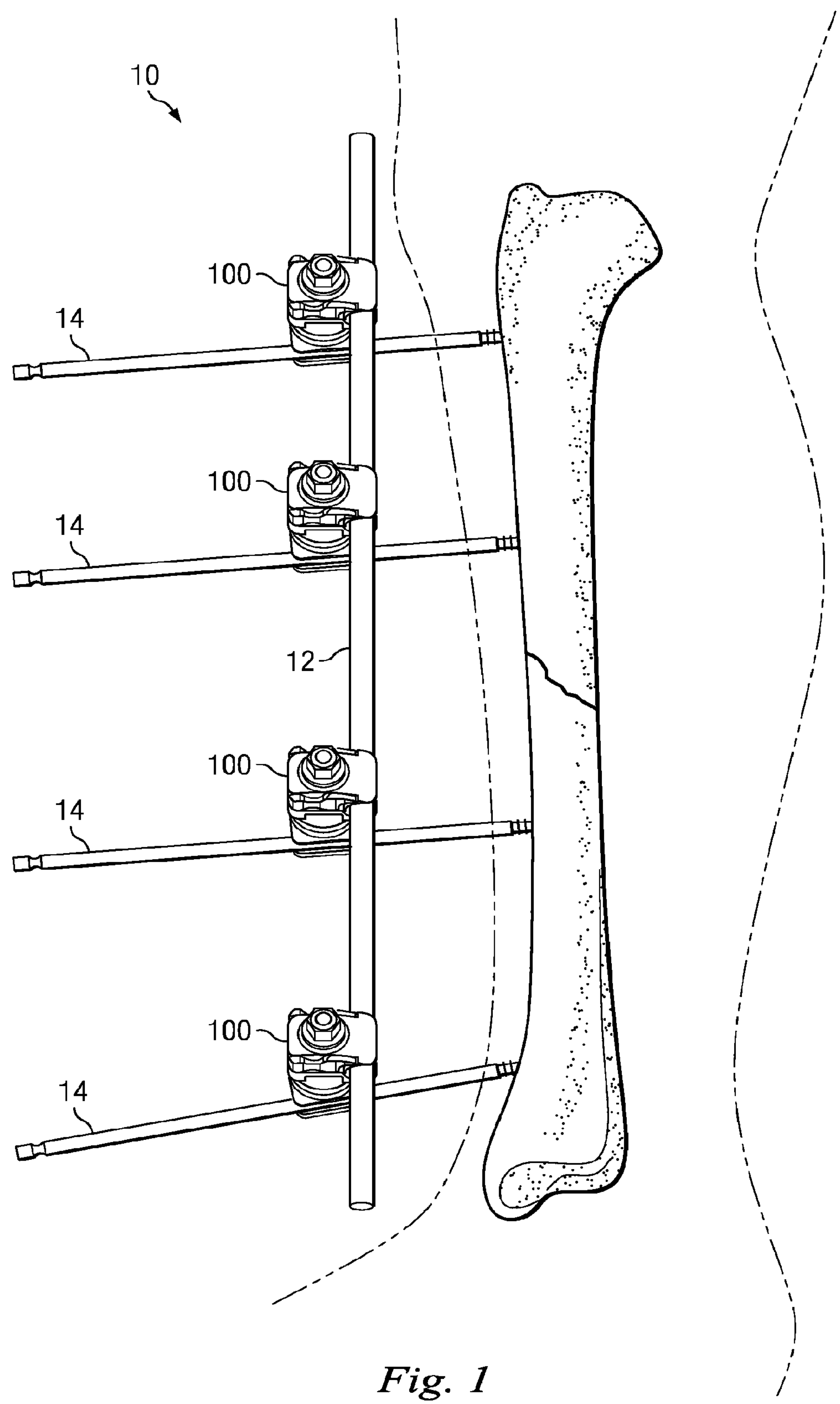
FIG. 1 is an illustration of an exemplary external fixation system in accordance with one exemplary aspect of the present disclosure connected to a patient's bone tissue.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure is directed to an external fixation clamping assembly that employs a gate mechanism that permits a health care provider to introduce a fixation element, such as a fixation rod or a bone pin, into the clamp but prevents its removal from the clamp unless a release mechanism is actuated. Once the fixation element is introduced through the gate into the clamp, it is provisionally held in the clamp in a manner allowing the clamp to be axially displaced or slid along the fixation element or rotated about the fixation element, while preventing removal of the fixation element. Using a locking system, the clamp can be fixed in place along the fixation element to prevent movement relative to the fixation element.

In one aspect, the external fixation system includes a plurality of clamps arranged to receive and secure fixation elements that extend into or support patient tissue. These multiple clamps are arranged to pivot relative to each other about an axis coincident with a longitudinally extending post, and in some embodiments are also arranged to swivel relative to each other about an axis coincident with a transverse axle. This increases simplicity and efficiency of fixation system setup.

FIG. 1 shows an exemplary external fixation system 10 attached to a patient's fractured tibia. The system 10 includes fixation elements as rigid bars 12 and pins 14 drilled into the bone on opposing sides of the fracture. Although this disclosure references bars and pins, it should be understood that any fixation element may be used, including bone pins, wires, rings, struts, bars, rods, or other structural members. In the example in FIG. 1, each pin 14 is received into one of the clamping devices 100 by inserting the pin 14 between facing jaws of a pin clamp of the clamping device 100. Likewise, the bar 12 is received into each of the clamping devices 100 by inserting the bar 12 between facing jaws of a bar clamp of each clamping device 100 as is described further below, to establish the external fixation framework for bone stabilization. In some embodiments, inserting the bar 12 or pin 14 places the clamp in a provisionally locked condition. In this position, the respective clamp can be rotated about the bar 12 or pin 14 and may be axially displaced along the bar 12 or pin 14. In addition, at least one of the clamps may rotate about a longitudinal axis of the clamping device 100, and may pitch up or down around the cylindrical axis of a saddle element, while the jaws maintain the bar or pin in the clamp. As remaining pins 14 are connected to the bar 12 using one of the clamping devices 100, the clamping devices may be adjusted to provide angulation and orientation necessary to align the bone for healing. Additional bar-to-bar fixation clamps and/or bar-to-pin fixation clamps may be added to expand and connect the frame as required. Some embodiments include multipin clamps. Once properly created, the frame may be locked by changing the clamp from a provisionally locked condition to the locked condition.

Figure 2:
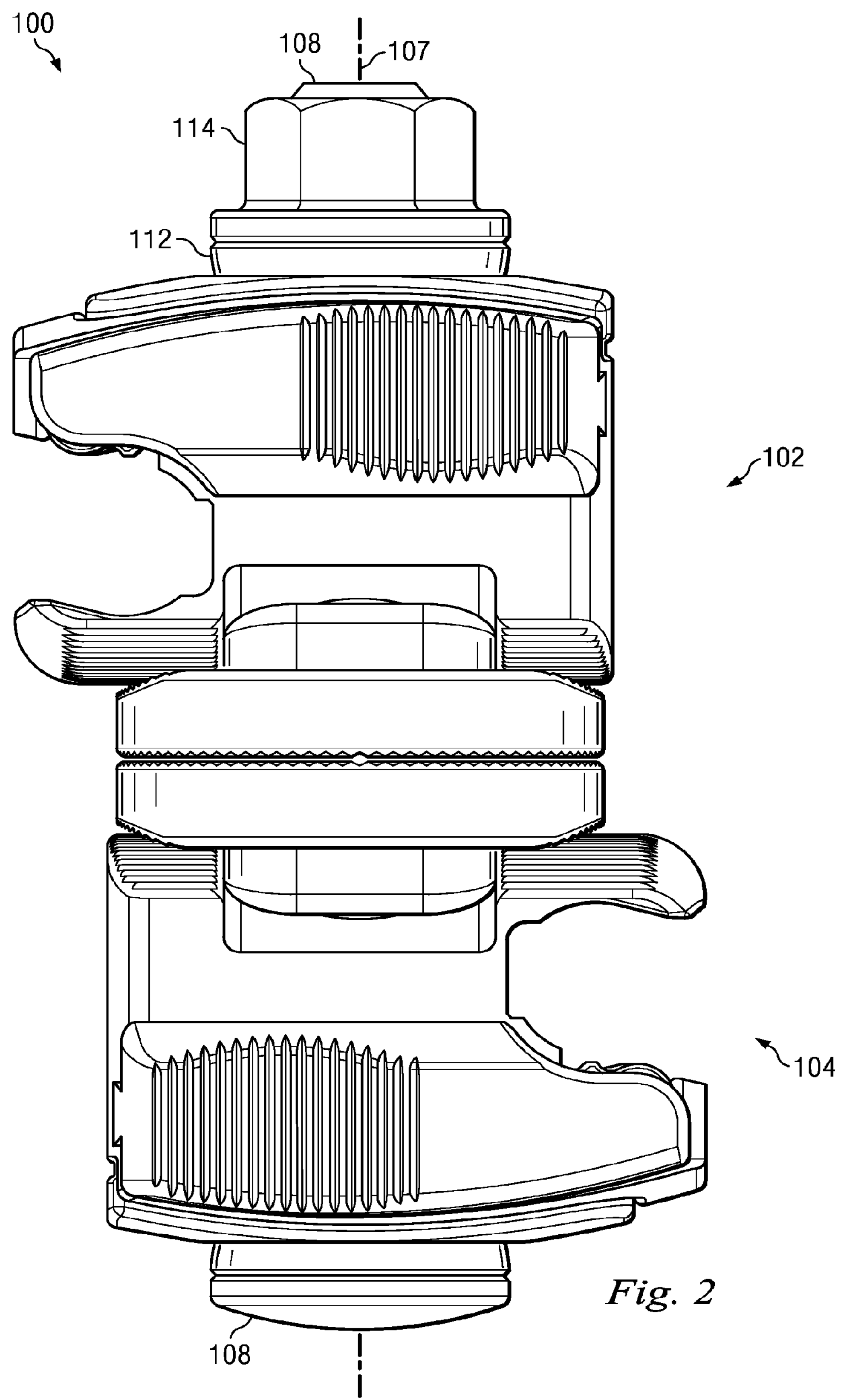
FIG. 2 is an illustration of an exemplary clamping assembly of an external fixation system according to one exemplary aspect of the present disclosure.

FIG. 2 illustrates an exemplary clamping assembly 100 according to one exemplary aspect of the present disclosure. The clamping assembly 100 includes a clamp 102 and an essentially identical clamp 104 that are structurally configured and arranged to clamp fixation elements. In this embodiment, the clamps 102 and 104 are essentially identical constructs conceptually and both may be considered bar clamps. However other clamping assemblies may employ pin clamps with the only significant differences involving dimensional changes to accommodate different fixation element diameters if required. In other embodiments, only one of the clamps may be used with alternative types of clamping constructs, including conventional single pin or bar clamping constructs, multi-bar or pin constructs, and other clamping systems. For example, in FIG. 1, the clamping assembly 100 may be formed of a first clamp dimensionally configured to capture and secure a fixation rod while the second clamp is dimensionally configured to capture and secure a bone pin. Each clamp 102, 104 independently receives and secures a bar, pin, or other fixation element. Other embodiments of the clamping device 100 include only a single bar or pin clamp on one end, with a multi-clamp set or other arrangement on the other end.

The bar clamps 102, 104 of the clamping assembly 100 provide multiple degrees of freedom, each operating independently of the other. For example, each clamp may pivot about a roll axis, a pitch axis, and a yaw axis in the clamp 102, 104. The roll axis is the axis of a bar or other fixation element within the clamps and about which the clamping device 100 may rotate. The pitch axis is a transverse axis about which the outer and inner jaws rotate relative to saddle components and/or the rest of the clamping assembly. The yaw axis is a longitudinal axis 107 defined by a post component or stud 108 and about which the clamp 102 can rotate relative to the clamp 104. The clamping assembly 100 is tightened onto a fixation element, and the clamp 102 is tightened to clamp 104 through tightening of a washer 112, a nut 114 and the post component 108 (all in FIG. 2), although other tightening methods are contemplated. The post component 108 includes a head (the top being visible in FIG. 2) and a shaft that extends through the clamping assembly to connect with the nut 106. The head of the post component 108 may be formed with a bowl-like surface shape, such as a spherical surface shape for example, that matches the spherical shape of the washer 112, which can be seen in FIG. 3. Alternatively, it may mate with a bowl-like washer like the spherical washer 112. In some embodiments, the post component does not include a head, but has two threaded ends that cooperate with two nuts for tightening the clamping assembly 100. Additional description of the axes and a post component or stud can be found in U.S. patent application Ser. No. 13/271,744 to Mullaney, filed Oct. 12, 2011, incorporated herein by reference. As used herein, the clamping side of each clamp 102, 104 is intended to mean the side of the clamp that receives the fixation element and the rearward side is the side opposite the side of the clamp receiving the fixation element. In FIG. 2, the clamping side of the clamp 102 is on the left and the clamping side of the clamp 104 is on the right.

Figure 3:
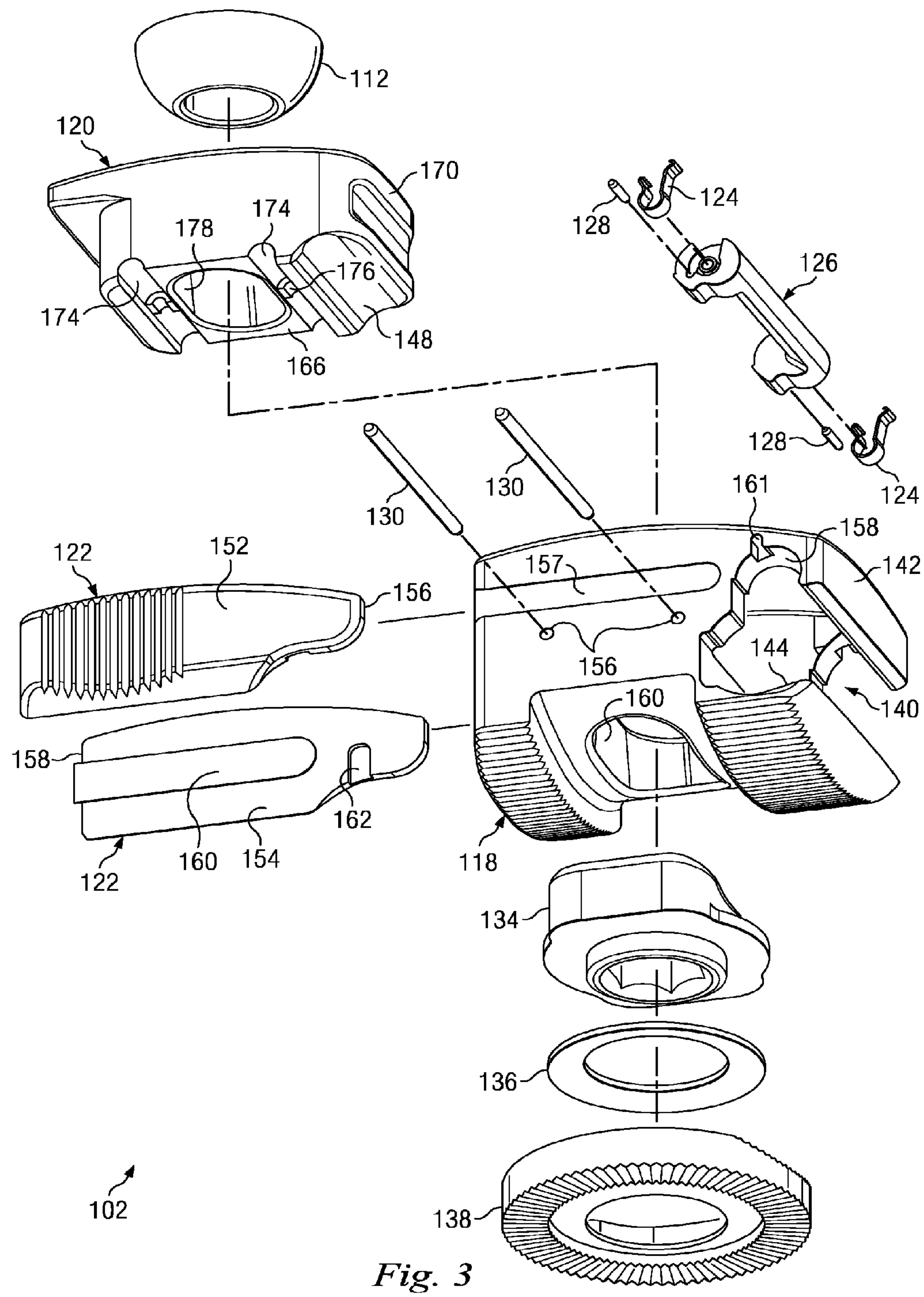
FIGS. 3 and 4 are illustrations of a clamp of the clamping assembly of FIG. 2 in an exploded configuration according to one exemplary aspect of the present disclosure.
Figure 4:
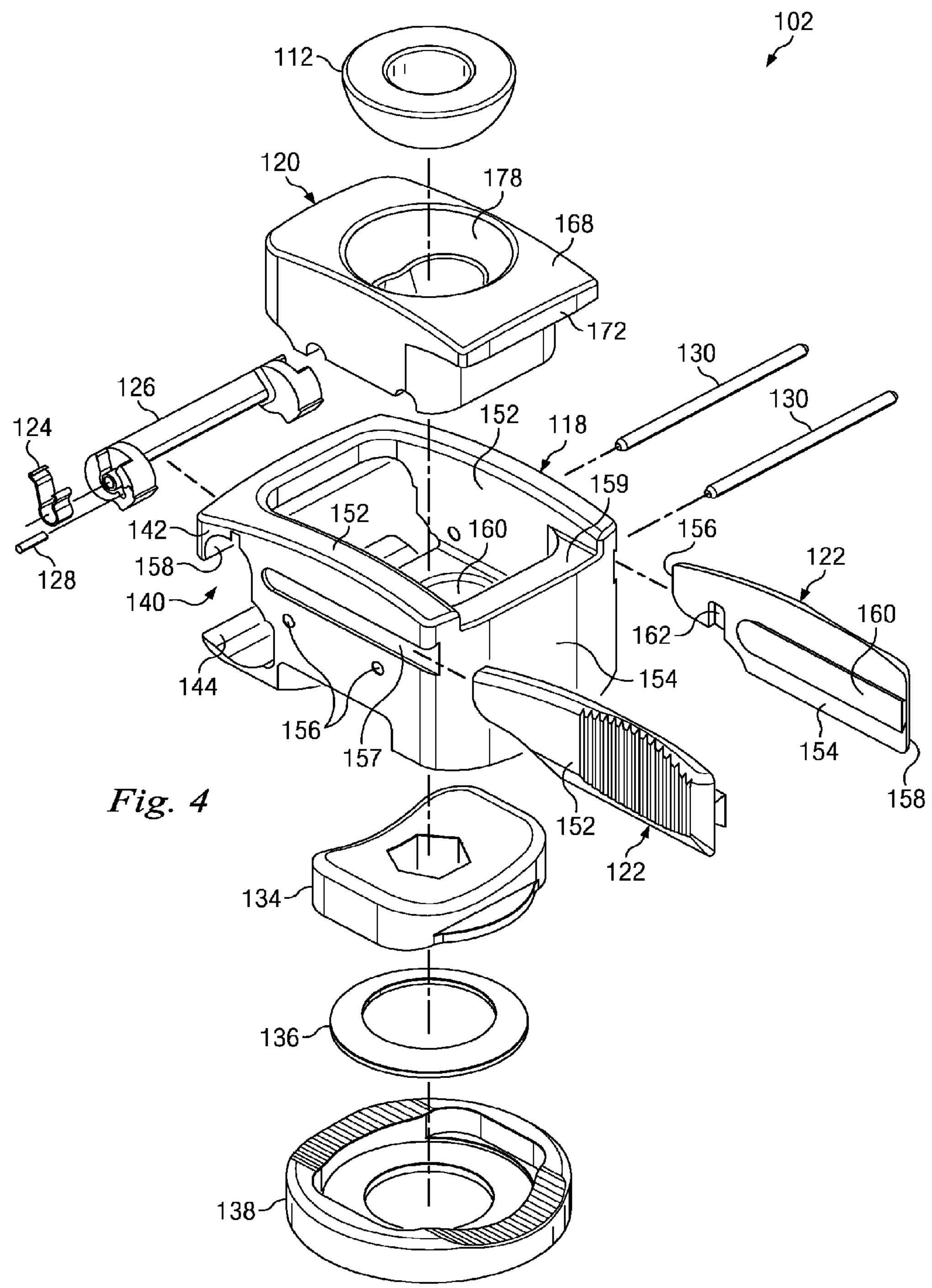
Figure 5C:
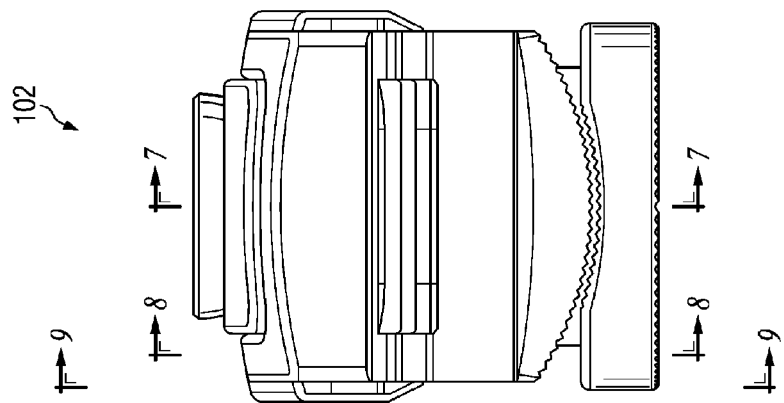
FIGS. 5A-5C are illustrations of the clamp of FIG. 3 showing a side view, a top view, and a back view respectively.
Figure 5A:
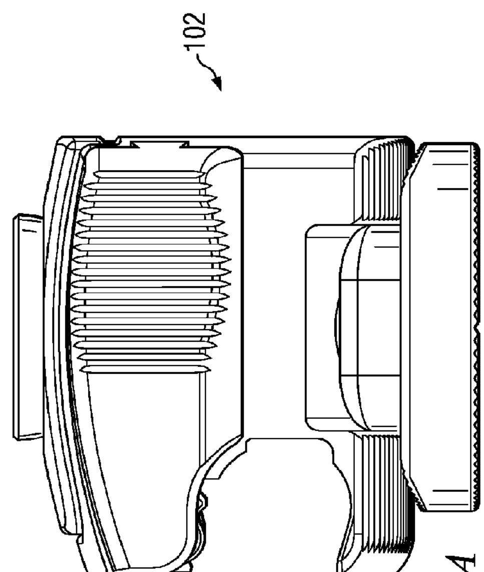
Figure 5B:
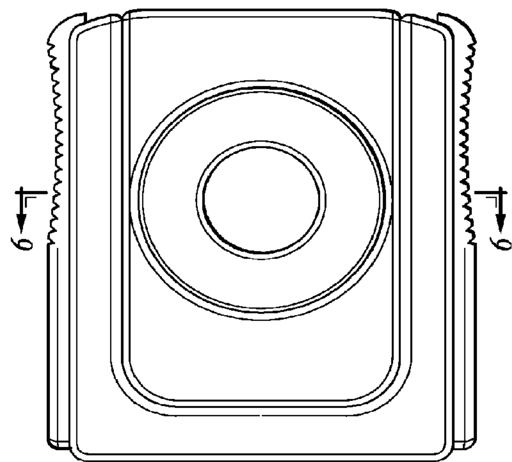

FIG. 2 shows a side view of the clamping assembly 100 and FIGS. 3 and 4 show different exploded views of the clamp 102. FIGS. 5A-5C respectively show a side view, a top view, and a rear view. FIGS. 6-9 are cross-sectional views taken through the respective lines 6-6, 7-7, 8-8, and 9-9 in FIGS. 5B and 5C.

Referring now to FIGS. 3 and 4, the clamp 102 includes an inner jaw 118 and an outer jaw 120. These jaws cooperate to capture the fixation element therebetween (shown in FIGS. 1 and 12A-12F). The clamp 102 also includes two sliders 122, two biasing elements or springs 124, a gate 126 which in this case is a revolving gate, two gate pins 128, and two spring wires 130. In addition, the clamp 102 includes a spacer 134, a spring washer 136, and a saddle 138. Detailed descriptions of the spacer 134, the spring washer 136, and the saddle 138 may be found in incorporated U.S. patent application Ser. No. 13/271,744, and therefore, they will not be described further here. It should be noted that the spacer 134, the spring washer 136, and the saddle 138 are not required to be part of the clamp 102, but are in place to provide an extra degree of articulation for each of the clamps 102 and 104. In some embodiments, these components are not present in the clamping assembly 100, and the inner jaw 118 of each of the clamps 102, 104 is configured to bear against the opposing inner jaw directly, removing the extra degree of freedom. In other embodiments, alternative pivoting elements provide the extra degree of freedom.

In this embodiment, the inner jaw 118 includes a body with a hollow center or recess arranged to receive the outer jaw 120, as is apparent in FIG. 4. In addition, the inner jaw 118 includes an opening 140 sized or arranged to receive a fixation element therethrough. The opening 140 is defined by a gate supporting portion 142 and a fixation element-contacting surface 144 that together form an opening between which the fixation element may be introduced. Because the fixation element contacting surface 144 is rigidly fixed relative to the gate supporting portion 142, the opening size between these elements of the inner jaw 118 is fixed and unchanging. The gate supporting portion 142 supports the gate 126. As will become apparent from the below discussion, although a fixation element may be introduced into the opening 140 in the inner jaw 118, the fixation element may be substantially held in place by the outer jaw 120, the inner jaw 118, and the gate 126.

In this example, the fixation element contacting surface 144 includes a transversely extending groove or slot that receives or engages the fixation element. The outer jaw 120 has a fixation element contacting surface 148 shown as a transversely extending groove or slot arranged to oppose the surface 144 of the inner jaw 118 and configured generally to hold the same fixation element. The contact surfaces 144, 148 may be shaped to generally correspond to the profile of the fixation elements, or may have shapes different than the profiles of the fixation elements. In some examples, the surfaces 144, 148 are configured to contact the fixation element at only particular locations, such as two locations each. In addition, in some embodiments, the recesses include teeth, cut-outs, or other features that interface with bars having a non-smooth or non-circular outer surface. In some examples, the jaws include flats on one or more of the jaws in place of the concave recesses.

Because of its hollow construct, the inner jaw 118 also includes side wall portions 152 and a rear wall portion 154. The gate supporting portion 142 forms the forward or clamping side wall portion of the recess of the inner jaw 118.

The side wall portions 152 include spring wire bores 156 extending therethrough. These bores 156 in each wall portion are aligned and arranged to permit the spring wires 130 to extend across and carry or suspend the outer jaw 120 within the inner jaw 118. In addition, the side wall portions 152 each include a dovetail groove 157 extending from the rearward side of the clamp toward the clamping side. This dovetail groove 157 is sized to interface and guide lateral displacement of the sliders 122. In addition, the side wall portions 152, near the clamping side of the clamp 102, includes a cutout shaped as a partial cylindrical bore 158 to capture and provide bearing for the revolving gate 126. In the embodiment shown, the partial cylindrical bore 158 extends beyond 180 degrees, capturing the revolving gate 126 and supporting it within the cylindrical bore 158. Adjacent the cylindrical bore 158, the inner jaw 118 includes a notch 161 for receiving the biasing elements or springs 124. As will be described below, the springs 124 bias the gate 126 to a closed or provisionally locked condition. The rear wall portion 154 includes an upwardly facing stop surface 159 that interacts with the outer jaw 120 during clamping to fully lock the fixation element.

A through hole 160 is configured to receive the post component 108, and in one embodiment, may allow the clamp 102 to pivot around the post component 108. It may also be shaped to allow the clamp 102 to rotate or pivot relative to the post component 108. Thus, the through hole 160 may have a rectangular shape, with rounded ends as shown in FIG. 3 and may include a conical component as shown in the cross-sectional view of FIG. 6. In other embodiments, the through hole 160 cooperates with the post component 108 to restrict relative rotation, while the clamp 104 and/or post component 108 is configured to permit relative rotation. In such an embodiment, the clamp 104 may rotate about the post component relative to both the post component 108 and the clamp 102 in the manner described in incorporated U.S. patent application Ser. No. 13/271,744.

The two sliders 122 are arranged to be disposed on opposing sides of the body of the outer jaw 120. The sliders 122 are disposed adjacent to and extend along the side wall portions 152. In this embodiment, the sliders 122 are independent of each other, and each has an outer facing surface 152, an inner facing surface 154 that faces the wall portions 152 of the inner jaw 118, a leading end 156 extending toward the clamping side of the clamp 102, and a trailing end 158. In the example shown, the outer facing surface 152 includes finger depressions formed therein for gripping by a user to slide the slider 122 within the dovetail groove 157 of the inner jaw wall portions 152. The inner facing surface 154 includes a dovetail portion 160 receivable in the dovetail groove 157 on the inner jaw 118 and configured to slide in the groove 157. The inner facing surface 154 also includes a pin slot 162 arranged to cooperate with the gate pins 128 to turn the revolving gate 126 to receive a fixation element or to permit removal of a fixation element.

The outer jaw 120 is sized to be received within the hollow in the inner jaw 118 and includes an inwardly facing surface 166, an outwardly facing surface 168, a clamping side end 170 that includes the groove or slot 148 for receiving the fixation element, and a rearward side end 172. The inwardly facing surface 166 includes spring grooves 174 configured to receive the spring wires 130. In the example shown, the spring grooves 174 includes a protruding central connector 176 that is configured to interface with the spring wires 130 in a central region. Contacting the spring wires 130 with the central connector 176 in a central region permits a relatively large amount of deflection that permits the upper jaw 120 to clamp onto and rigidly secure the fixation element within the clamp 102 when the clamp is placed in a fully locked condition. The rearward side end 172 of the outer jaw 120 includes a projecting stop arranged to extend over and interface with the stop surface 159 of the inner jaw 118. This positive and hard engagement permits the upper jaw to be tightened onto a fixation element to secure the fixation element in the fully locked condition.

Figure 6:
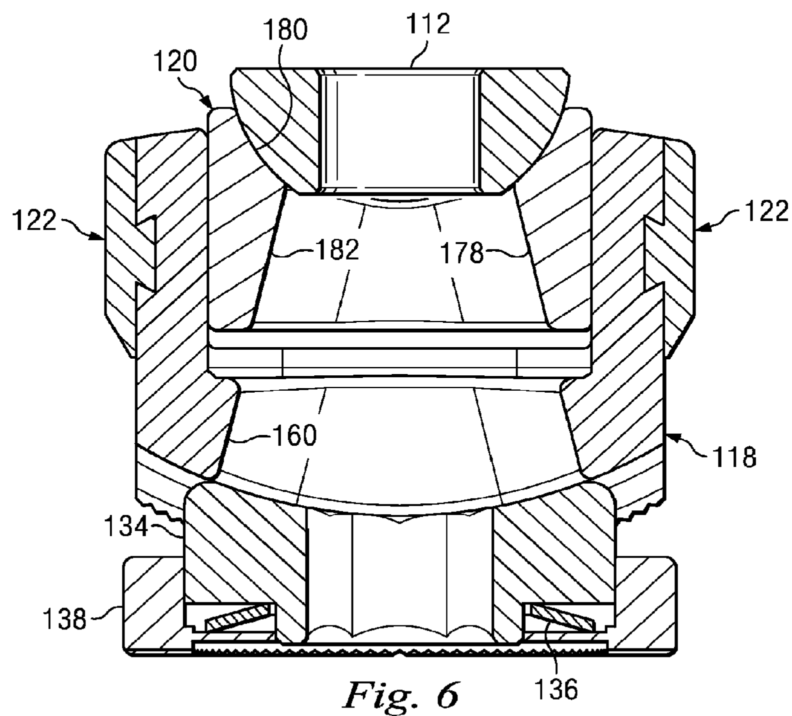
FIG. 6 is an illustration of a cross-section of the clamp of FIG. 5B taken through the lines 6-6 in FIG. 5B according to one exemplary aspect of the present disclosure.
Figure 7:
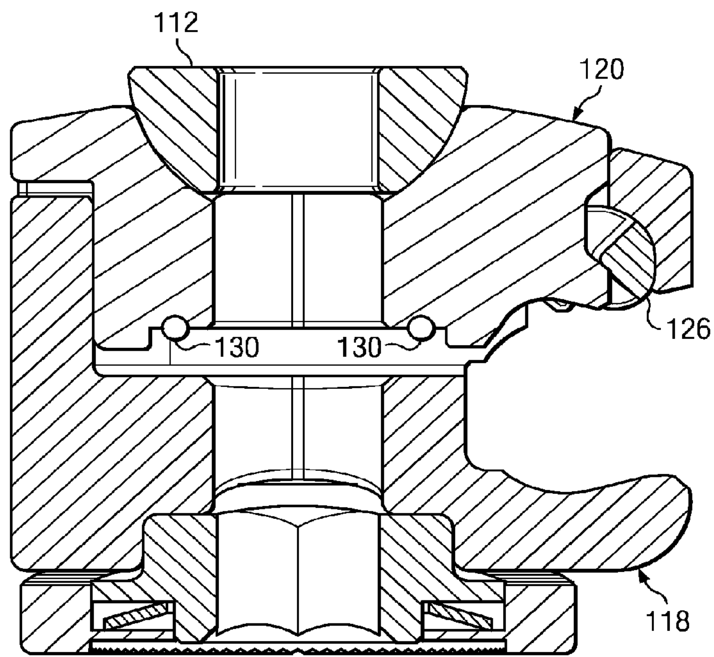
FIG. 7 is an illustration of a cross-section of the clamp of FIG. 5C taken through the lines 7-7 in FIG. 5C according to one exemplary aspect of the present disclosure.
Figure 8:
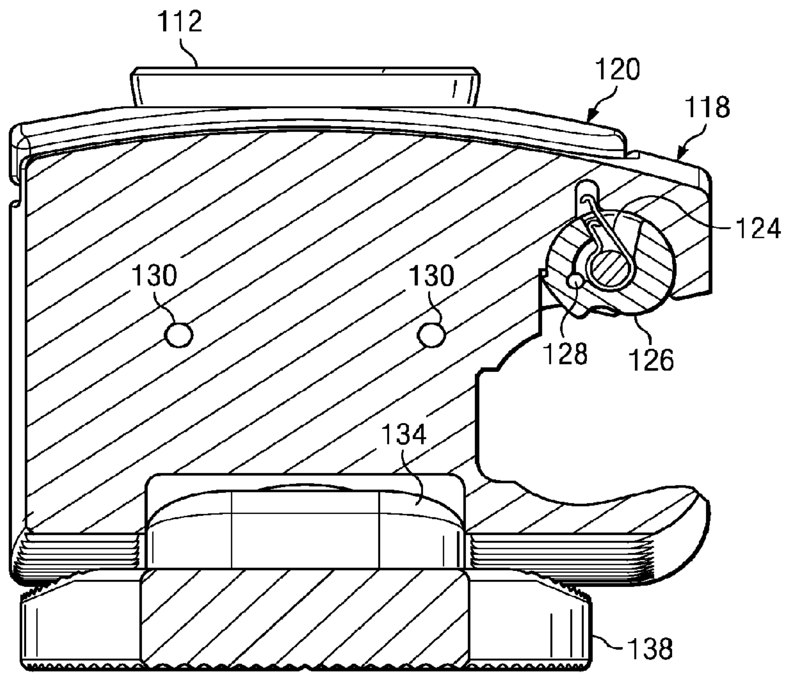
FIG. 8 is an illustration of a cross-section of the clamp of FIG. 5C taken through the lines 8-8 in FIG. 5C according to one exemplary aspect of the present disclosure.
Figure 9:
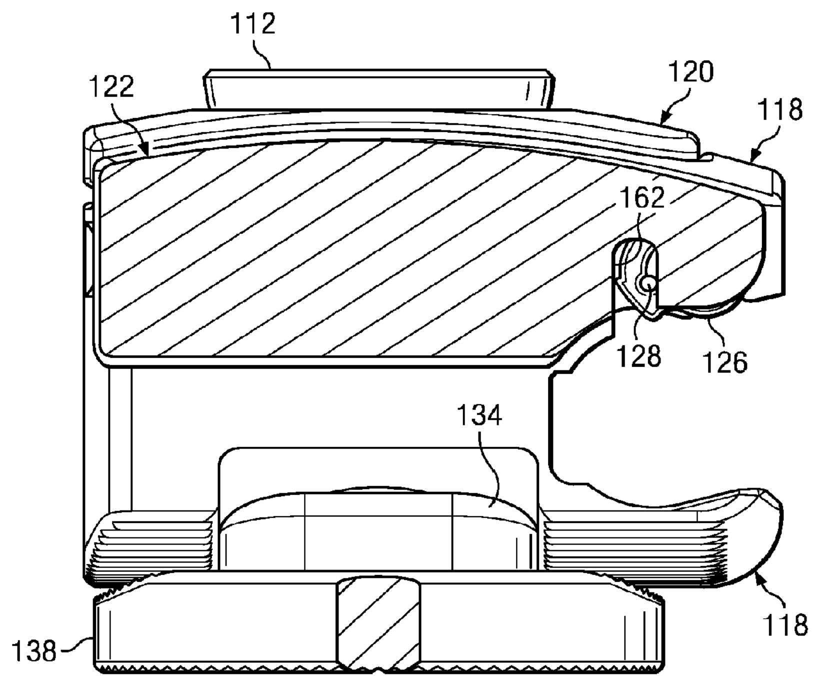
FIG. 9 is an illustration of a cross-section of the clamp of FIG. 5C taken through the lines 9-9 in FIG. 5C according to one exemplary aspect of the present disclosure.

The outer jaw 120 includes a through hole 178 with a spherical top portion 180 and a rectangular, but conically shaped bottom portion 182, that can be seen in FIGS. 3 and 6. The spherical top portion 180 is arranged to cooperate with and receive the spherical washer 112.

The spring wires 130 are suspended across the hollow center or recess in the inner jaw 118 through the spring wire bores 156 formed in either side of the inner jaw 118. The outer jaw 120 is sized and shaped to be received into the hollow center or recess and bears on the spring wires 130 at the midline of the inwardly facing surface 168 of the outer jaw 120. Alternative biasing elements, such as for example, coil springs, helical wire springs, leave springs, elastomeric materials and dampening members, along with many other approaches are also contemplated.

A biasing element 124 provides a torsion load about an axis of the revolving gate 126 against the notch 161 in the inner jaw 118 acting to rotate the revolving gate 126 about its axis in a counter clockwise direction. The gate 126 includes end portions with recesses configured to receive the spring 124, and cooperates with the spring 124 to bias the gate 126 to a blocking position or a removal-preventing position shown in FIG. 10. This blocking or removal preventing position may be referred to as a provisionally locked condition that does not fully lock the fixation element in place, but prevents removal of the fixation element, while allowing the clamp assembly 100 to still be slid along or rotated about the fixation element during fixation frame set up. In the embodiment shown, the biasing element spring 124 is formed of flat wire but other biasing elements or alternatively shaped elements such as helically wound torsion springs, torsion bar springs, leaf springs acting on a cam surface, spring loaded plungers acting on a cam surface, along with many other approaches are also contemplated choices that are primarily driven by packaging constraints for the design in question.

Figure 10:
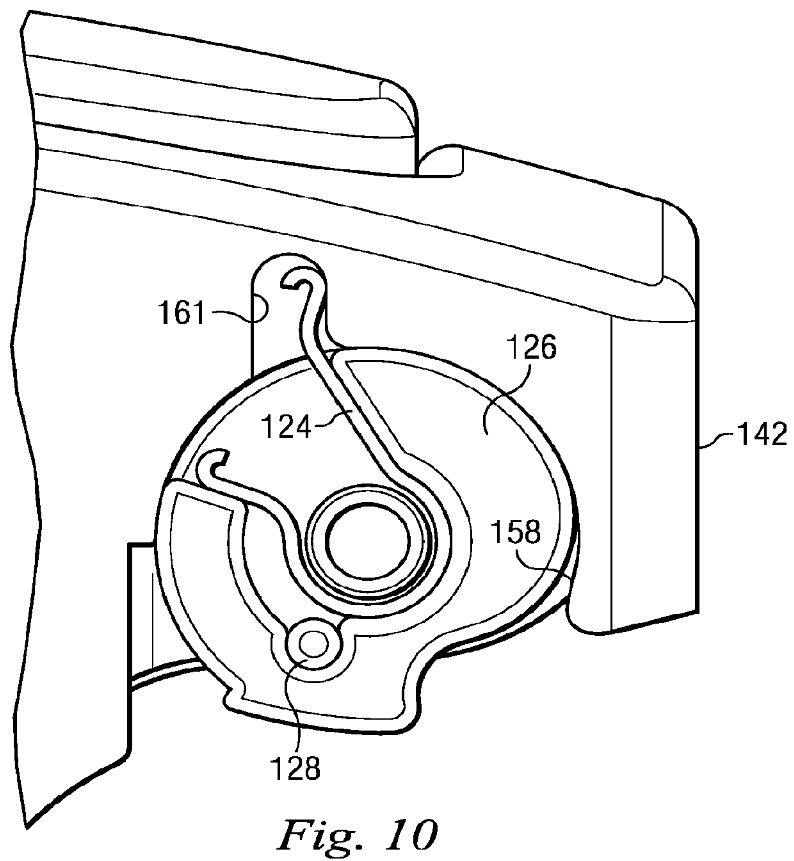
FIG. 10 is an illustration of a gate of the clamp in of FIGS. 3 and 4 according to one exemplary aspect of the present disclosure.
Figure 11:
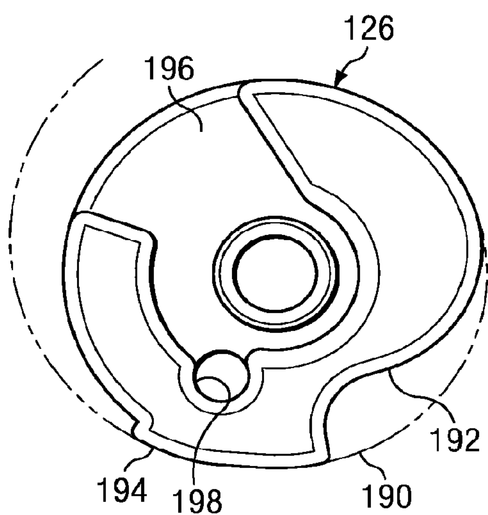
FIG. 11 is an illustration of the gate of FIG. 10 with reference lines according to one exemplary aspect of the present disclosure.

FIGS. 10 and 11 show end views of the revolving gate 126. The revolving gate 126 includes a recess 196 formed therein for receiving the biasing elements 124 and includes a pin bore 198 for receiving the gate pins 128. The recess 196 is formed by inner walls that are acted upon by the biasing elements 124 and includes a gap in the walls through which the biasing element 124 can extend and engage the notch 161 of the inner jaw 118. FIG. 10 shows the biasing elements 124 and the gate pins 128 in place in the gate 126. The biasing element 124 is arranged to bias the gate 126 to a closed position, where the gate 126 protrudes into the opening of the clamp 102, preventing removal of a fixation element held in the clamp 102. The gate pin 128 protrudes from the gate 126 and fits within the pin slot 162 in the slider 122. A user can displace the gate pin 128, and thereby rotate the gate 126, by sliding the slider 122 so that the pin slot 162 in the slider pushes the gate pin 128, forcing the gate 126 to revolve around its axis.

Referring now to FIG. 11, the revolving gate 126 has a primarily cylindrical configuration as indicated by the diameter reference line 190 with a relief cut 192 and a spiral or ramped surface 194 tangent to the cylindrical configuration. The relief cut 192 allows passage of the fixation element 12 when the revolving gate 126 is rotated into a particular position. The ramp 194 allows a progressive lessening of the distance between the outer surface of the revolving gate 126 and the fixation element contacting surface or slot 144 of the inner jaw 118 such that the torsional loading of the biasing element spring 124 can provisionally clamp the fixation element 12.

In this embodiment, the gate 126 is disposed within the partial cylindrical bore 158 of the gate supporting portion 142 of the inner jaw 118. Flappers, check valves, draw bridges, and swinging or hinged doors all fall within this category of rotating gates. Alternative approaches are also envisioned that would utilize a sliding gate as opposed to a revolving one much like that of a jail cell or pocket door, again the function would largely be the same, with the sliding gate sliding to a first position to receive a fixation rod in the clamp, and sliding to a second position to prevent removal.

Figure 12A:
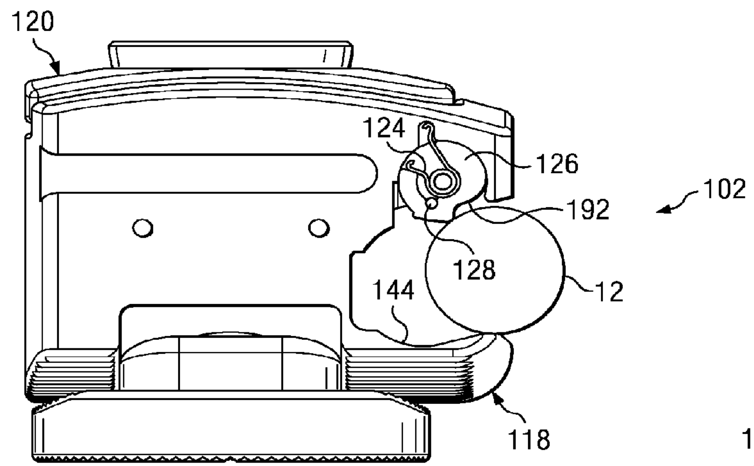
FIGS. 12A-12F are series of illustrations of the clamp of FIGS. 3 and 4 with a fixation element being introduced into the clamp and being removed from the clamp.

The sequence of insertion and removal of the fixation element 12 will be described with references to the series of FIGS. 12A-12F. The insertion procedure will be first described with reference to FIGS. 12A-12C and the removal procedure will be described with reference to FIGS. 12D-12F. Describing the insertion procedure, the clamp 102 of the clamping assembly 100 can be held stationary in any manner. For example, the sliders 122 can be pinched or any portion of the assembly 100 can be so handled as to hold the assembly fixed against the forces generated during the insertion process. In this condition, referred to herein as the starting condition, the ramp 194 projects into the pathway of the fixation element. The ramp 194 and the inner jaw 118 are particularly sized and shaped so that the distance between the ramp 194 and the fixation element contacting surface 144 of the inner jaw 118 is less than the diameter of the fixation element 12. As a fixation element 12 is pressed into the opening in the clamp 102, it comes into contact with the leading edge of the relief cut 192 in the revolving gate 126 as shown in FIG. 12A. This pressure forces the revolving gate 126 to rotate about its axis in opposition to the biasing element spring 124.

Figure 12B:
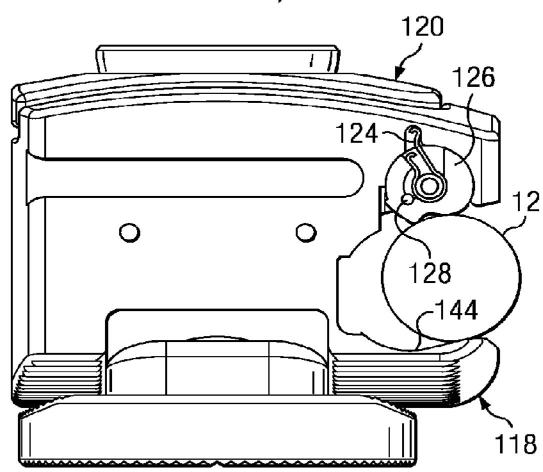

FIG. 12B shows the gate 126 rotated due to forces applied by the fixation element 12 so that the relief cut 192 allows entry of the fixation element 12 into the jaw slot 144 of the inner jaw 118. Continued advancement of the fixation element 12 through the opening 140 in the clamp 102 eventually moves it into the clamp beyond the gate 126. During this time, the gate 126 continues to rotate until rotation is no longer required to permit the fixation element 12 to pass. This condition is referred to herein as the open condition, where the ramp 194 is in a condition permitting the fixation element to pass into and seat in the clamp 104. Accordingly, in this open condition, the distance between the ramp 194 and the fixation element contacting surface 144 of the inner jaw 118 is equal to or greater than the diameter of the fixation element 12. Since the biasing spring 124 continuously applies a biasing force to move the gate 126 to the starting condition, the gate 126 begins to return toward the starting condition as the fixation element 12 continues to move further into the clamp beyond the gate 126. Eventually, when the fixation element 12 is advanced into the clamp deeply enough to provide clearance, the biased gate 126 returns far enough toward the starting condition to physically or mechanically interfere with the fixation element in a manner preventing removal of the fixation element 12 from the clamp 102, in a provisionally locked condition. In some embodiments, the gate 126 returns to the starting condition to prevent removal of the fixation element 12 from the clamp 102. In these embodiments, the provisionally locked condition is the same condition as the starting condition. In other embodiments, the gate 126 only partially returns toward the starting condition, but still displaces enough to create the physical or mechanical interference to prevent removal of the fixation element 12 from the clamp 102. In these embodiments, the provisional locking condition is a location between the starting condition and the locking condition.

Figure 12C:
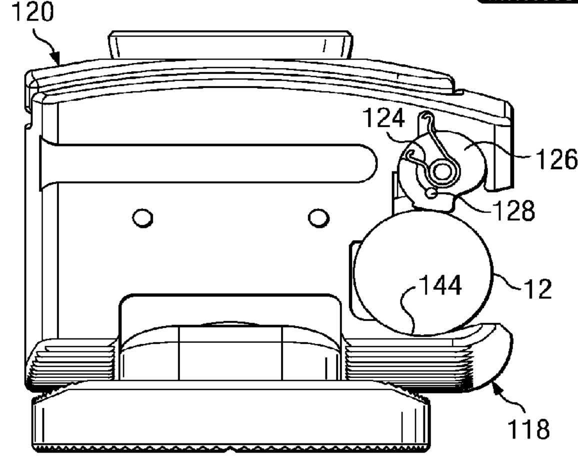

FIG. 12C shows the fixation element 12 seated in the fixation element contacting surface 144 and the revolving gate 126 is shown rotated back into its initial location or starting condition. As can be seen, the ramp 194 of the gate 126 is now disposed to interface with the fixation element 12 and prevent its removal. The spiral or sloped nature of the outer profile of the ramp 194 provides a provisional clamping load onto fixation element 12. It should be noted that in this configuration, forces acting to remove the fixation element 12 would tend to force a further counterclockwise rotation or a generally vertical displacement, from the perspective shown in FIG. 12C, due to the spiral or sloped nature of the outer profile of the ramp 194, thus preventing the removal of fixation element 12.

As shown in FIG. 12C, the fixation element 12 is physically blocked or secured within the clamp 102 in a provisional lock. A provisional lock as used herein is a clamp locking condition that prevents removal of the fixation element from the clamp, but the clamp loosely secures the fixation element such that the fixation element may be axially slid relative to the clamp or the clamp may be rotated about the fixation element 12. This provisional condition allows a surgeon to snap the clamp assembly 100 onto a fixation element, but still manipulate or adjust the clamp assembly position relative to the fixation element.

Figure 12D:
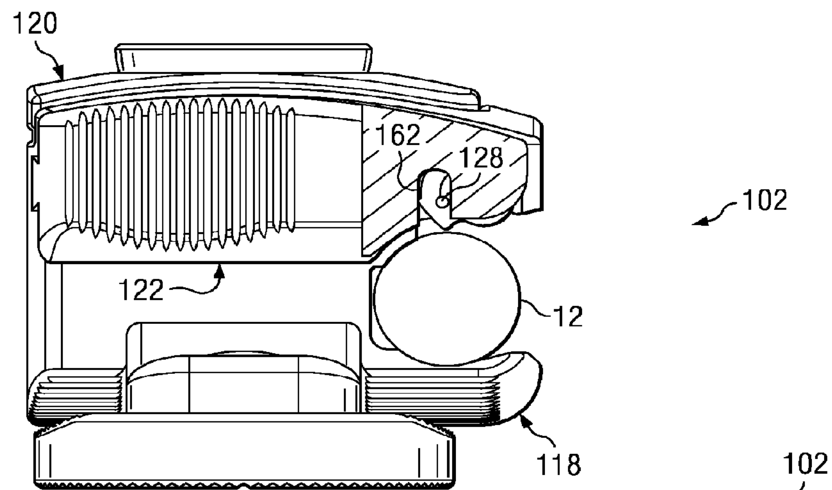
Figure 12E:
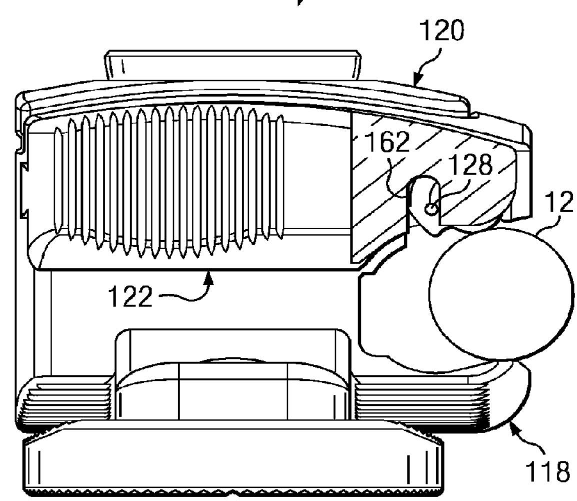
Figure 12F:
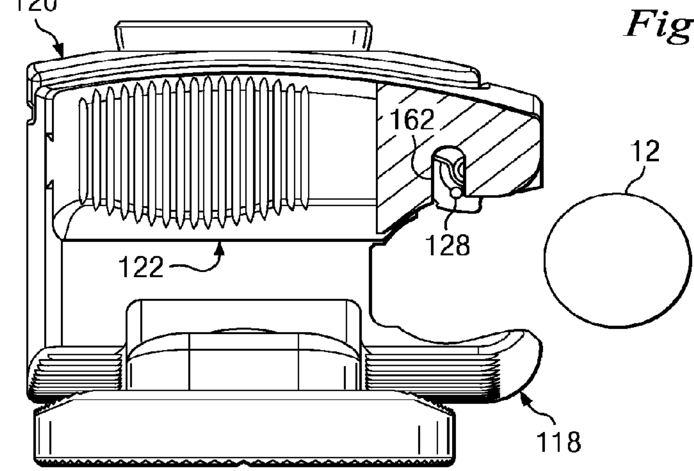

The removal structure and operation will now be described with reference to FIGS. 12D-12F. FIGS. 12D-12F show partial cross-sections taken through the slider 122. The gate pins 128 are disposed within the pin slots 162 milled in the sliders 122. Therefore, while free to slide within the dovetail groove 157 in the inner jaw 118 as shown in FIGS. 4 and 6, the movement also drives the gate pins 128. This in turn rotates the gate 126.

In the normal operating condition, the gate pins 128 lie within the pin slot 162. As can be seen in FIG. 10, the gate pins 128 are offset from a central axis through the gate 126, but extend in a direction parallel to the central axis. Accordingly, during rotation of the gate 126, the gate pins 128 rotate along an arcing pathway. The pin slots 162 are wide enough to permit the gate pins 128 to rotate without interference from the edges of the pin slot 162 as the gate 126 revolves between the starting condition and the open condition. However, as described below, the pins 128 and pin slots 162 interfere to manually rotate the gate 126 in order to release the fixation element 12.

Depending upon the embodiment, sliding the sliders 122 and their pin slots 162 back away from the fixation element 12 forces the trailing edge of the milled pin slot 162 to come into contact with the revolving gate pins 128. This pressure forces a clockwise rotation of revolving gate 126 such that the relief cut 192 is rotated into an orientation that allows passage of fixation element 12 as shown in FIG. 12D. FIG. 12E shows the fixation element 12 partially out of the jaw recess, and FIG. 12F shows it completely clear of the jaw recess. It should be noted that the pin slot 162 has sufficient width as to not prevent the revolving gate 126 from rotating clockwise due to pressure applied during the insertion process. This aspect of the design is to insure that holding the clamp assembly by the sliders 122 will not prevent the acceptance of fixation element 12.

Referring to FIG. 2, the process of placing the clamping assembly 100 in fully locked condition will be described. In this embodiment, the stud or post component 108 passes entirely through the clamping assembly 100. Tightening the nut 114 lessens the distance between the nut 114 and the head of the stud or post component shown in FIG. 2. This lessening of that distance forces the spherical washer 112 against the outer jaw 120 which in turn forces the outer jaw 120 closer to the inner jaw 118 lessening the distance between the fixation element contacting surface 148 in the outer jaw 120 and the fixation element contacting surface 144 in the inner jaw 118 which provides a fully locked clamping load on the fixation element 12. Accordingly, tightening the nut 114 results drives the outer jaws into the inner jaws, deflecting the spring wires 130 until the outer jaw is secured against the stop surface 159 on the rear wall portion 154 of the inner jaw and secured against the fixation element. Since the force is applied between the stop surface 159 and the fixation element, any further tightening only increases the clamping load and further tightens on and secures the fixation element. Opposing this action are the spring wires 130 which are shown in the undeflected state for clarity in FIGS. 3 and 4 with respect to the central connectors 176 of the outer jaw 120. The spring wires 130 have a fairly low spring rate and simply serve to return the outer jaw 120 to the open state upon loosening the nut 114. This rate should be tailored to allow for a variable amount of friction as a function of torque on the nut 114 such that the resistance to motion of the fixation element 12 can be adjusted to facilitate gross manipulation of the clamping assembly 100 without such a high degree of force being applied such that the serrations on the saddle 138 become engaged with the saddle and/or the inner jaws 118. To facilitate this action, a high rate spring washer 136 may be used between opposing saddles 138 and their mating inner jaws 118. Additional details of high spring rate spring washers may be found in incorporated U.S. patent application Ser. No. 13/271,744 to Mullaney, filed Oct. 12, 2011. In summary, positively clamping fixation element 12 comes in two stages, the first utilizes a lesser torque on the nut 114 causing the outer and inner jaws 120 and 118 to deflect spring wires 130 such that slots 148 and 144 clamp the fixation element 12 over some range of clamping force that is in proportion to torque on nut 114. At a higher torque threshold, the force becomes sufficient to collapse the spring washers 136 allowing the serrations on opposing saddles 138 and the inner jaws 118 to come into engagement positively locking the construct in a fixed state.

It is worth noting that in the embodiment described above, the clamp assembly 100 secures the fixation element 12 at least in a provisionally locked condition without actual displacement of the outer jaw 120 relative to the inner jaw 118. As is apparent from the discussion above, the gate 126 adjusts in a manner relative to one of the inner and outer jaws 118, 120 to change the size of the fixation element-receiving opening, without requiring relative displacement of the inner and outer jaws 118, 120. In the embodiment shown, only when the clamp condition is changed from the provisionally locked condition to the fully or final locked condition do the inner and outer jaws 118, 120 move relative to one another.

In yet other embodiments, the gate 126 is arranged as a revolving turn-style gate that revolves around an axis to allow passage of the fixation element. Accordingly, in this embodiment, the turn-style gate rotates between an open position and a closed position, without the gate returning to the closed condition. Instead, the gate is structurally configured such that as the gate rotates to allow the fixation element into the clamp, a blocking portion of the gate simultaneously rotates into a blocking position behind the fixation element. Other embodiments are also contemplated.

Although shown with gate pins at both ends, some embodiments have a single gate pin. Therefore, in those embodiments, actuation of only a single slider may be required to rotate the revolving gate and open the clamp.

FIGS. 13-20 disclose another embodiment of a clamping device 300 according to an aspect of the present disclosure. As will become apparent from the discussion below, some of the elements of the clamping device 300 are similar to those of the clamping device 100 described above with reference to FIGS. 1-12. The description of the structure and methods relevant to elements similar to or exactly like those described above may not be repeated in the description below, as the description above already applies equally to those components. Likewise, any additional features or functionality described below may apply to the elements described above.

Figure 13:
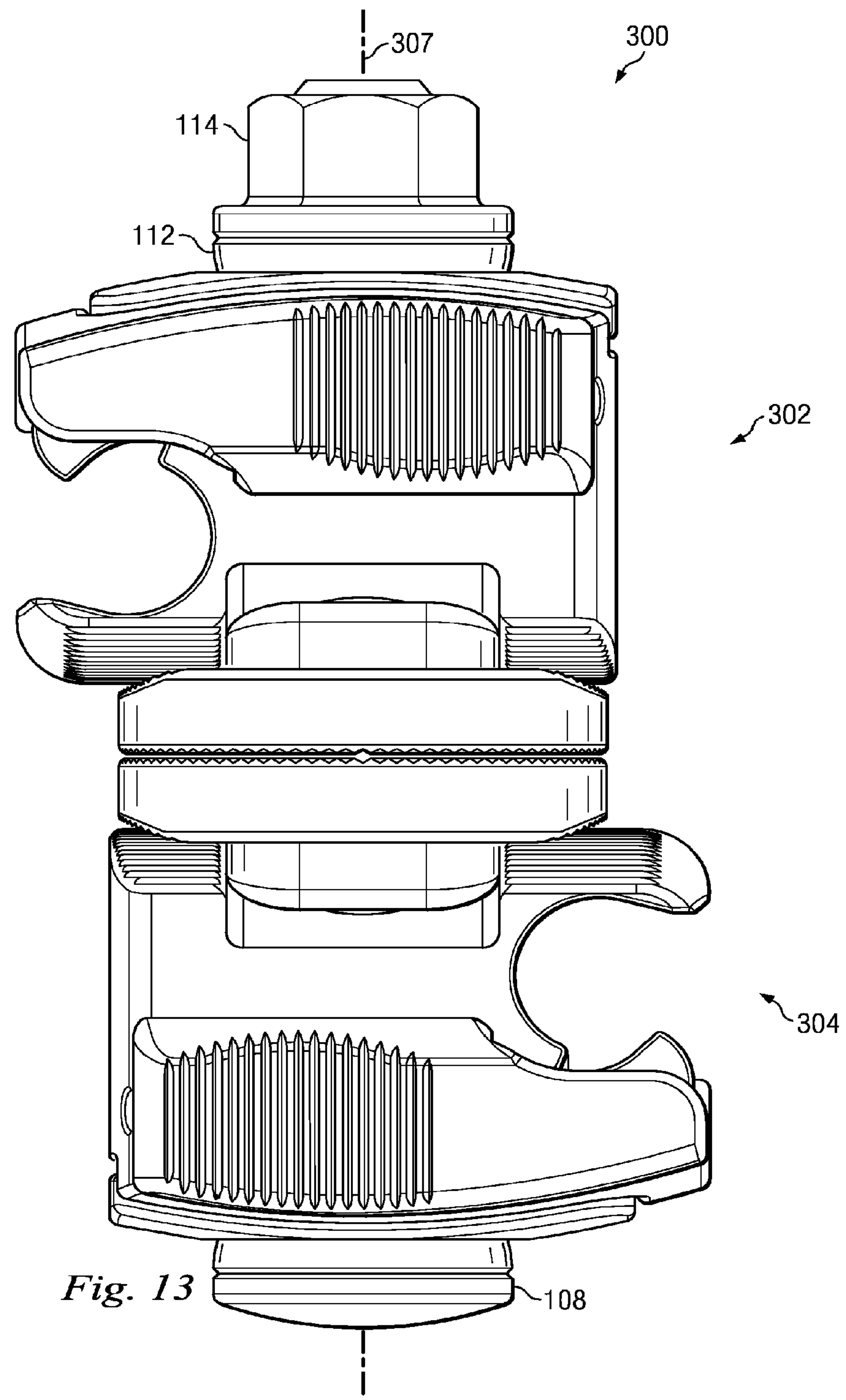
FIG. 13 is an illustration of another exemplary clamping assembly of an external fixation system according to an exemplary aspect of the present disclosure.

FIG. 13 illustrates an exemplary clamping device 300, made up of first and second clamps 302, 304 that are structurally configured and arranged to clamp fixation elements, such as the external fixation rod 12 or bone pin 14 shown in FIG. 1. As can be seen, this embodiment also includes a post component or stud 108, a nut 112, and a spherical washer 114.

Here the clamps 302, 304 are essentially identical constructs conceptually with the only significant differences involving dimensional changes to accommodate different fixation element diameters if required. In other embodiments, only one of the clamps may be used with alternative types of clamping constructs, including conventional single pin or bar clamping constructs, multi-bar or pin constructs, and other clamping systems. Since the clamps in this example are substantially identical, only the clamp 302 will be described in detail.

Referring to FIGS. 14-19, exemplary clamp 302 includes an inner jaw or main body 318, an outer jaw 320, two sliders 322, two springs 324 with associated followers 325, a revolving gate 326, gate pins 328, and two spring wires 130. The clamp 302 also includes the spacer 134, the spring washer 136, and the saddle 138.

The inner jaw 318 in this embodiment has many of the same features as the inner jaw 118 described above, including a body with a hollow center or recess arranged to receive the outer jaw 320. In addition, the inner jaw 318 includes a gate supporting portion 342, and a fixation element-contacting surface 344 with an extended recess or slot that together form an opening 340 into which the fixation element may be introduced. Because the fixation element contacting surface 344 is rigidly fixed relative to the gate supporting portion 342, the opening size between these elements of the inner jaw 318 is unchanging or fixed. The gate supporting portion 342 supports the gate 326. As is apparent from the below discussion, although a fixation element may be introduced into the opening in the inner jaw 318, the fixation element may be substantially held in place by the outer jaw 320, the inner jaw 318, and the gate 326. The two sliders 322 are arranged to be disposed on opposing sides of the body of the outer jaw 318.

Referring to FIGS. 14-19, the inner jaw 318 includes side wall portions 352 with spring wire bores 356, a dovetail groove 357, a partial cylindrical bore 358 that captures and provides bearing for the revolving gate 326, and a spring biasing groove or slot 359. In the embodiment shown, the partial cylindrical bore 358 extends beyond 180 degrees, capturing the revolving gate 326 and supporting it within the cylindrical bore 358. The spring biasing groove or slot 359 is arranged to partially receive a biasing spring that cooperates with the slider 322 as discussed further below.

The outer jaw 320 includes a fixation element contacting surface 348 shown as a groove or slot that cooperates with the fixation element contacting surface 344 of the inner jaw 318 to receive and secure the fixation element. The spring wires 130 are suspended across the hollow center or recess in the inner jaw 318 through holes drilled in either side of the inner jaw 318 in the manner discussed above. The outer jaw 320 is sized and shaped to be received into the hollow center and bears on the spring wires 130 at the midline of the lower surface of the outer jaw 320. In this embodiment, the outer jaw 320 includes two biasing bore holes 366 extending from the leading end or the clamping side of the outer jaw 320. The bore holes 366 are sized and arranged to house the biasing spring 324 and the follower 325 in a position that aligns the follower 325 with a cam surface on the gate 326. This can be seen in the cross-section of FIG. 18.

The sliders 322 include an outer facing surface 352, an inner facing surface 354, a leading end 356 and a trailing end 358. The inner facing surface 354 includes a dovetailed portion 360, a pin groove 362, and a biasing groove 364. The dovetailed portion 360 interfaces with the dovetailed groove 357 in the inner jaw 318 allowing the slider 322 to slide axially within the groove relative to the inner jaw 318. The pin groove 362 is a non-linear groove that interfaces with the gate pins 328 to guide the gate pin 328 along with its associated gate 326. The biasing groove 364 is sized to receive a biasing spring 370 with a ball 372 at each end to bias the slider 322 to a central position relative to the inner jaw 318. Through the pin groove 362, the biasing spring 368 may bias the gate pin 328 and the gate 326 to a particular position to secure a fixation element within the clamp 302. When the slider 322 is positioned on the inner jaw 318, the biasing groove 364 in the slider aligns with the spring biasing groove or slot 359 in the inner jaw 318, and the spring 368 and balls 370 are disposed in both the spring bias groove 364 and the spring biasing groove or slot 359.

The revolving gate 326 includes a cam surface 380, and pin bore holes 382 disposed in gate ends. The pin bore holes 382 receive the gate pins 328. The revolving gate 326 is primarily a cylindrical configuration with a relief cut 384.

The biasing element springs 324 within the outer jaw 320 provide compressive loads on the followers 325 which bear against the cam surface 380 of the revolving gate 326. Since the contact normal between the follower 325 and the cam surface 380 is offset from the axis of rotation of the revolving gate 326, a rotation force is generated acting to rotate the revolving gate 326 in a clockwise direction. In the example shown, the biasing element spring 324 is a helical compression spring acting on the follower 325 and the cam surface 380, but other approaches such as flat wire torsion springs, torsion bar springs, along with many other approaches are also contemplated choices, and these are primarily driven by packaging constraints.

The relief cut 384 allows passage of the fixation element 12 when the revolving gate 326 is rotated into a particular position, such that a portion of the gate 326 provides a progressive lessening of the distance between the door 326 and the contacting surface 344 of the inner jaw 318 such that the torsional loading of the biasing element spring 324 can provisionally clamp the fixation element 12. The loading of the biasing element spring 324 can provisionally clamp the fixation element 12 into the clamp 302 as it applies a pinching load acting on the gate 326 to retain the gate 326 in place, thereby provisionally clamping the fixation element 12 between the leading edge of revolving gate 326 and the contacting surface 344.

In this embodiment, the gate 326 is disposed within the partial cylindrical bore 358 of the gate supporting portion 342 of the inner jaw 318. The cylindrical nature of the revolving gate 326 simply implies that an axis of rotation is involved in this embodiment. Flappers, check valves and draw bridges all are contemplated alternatives falling within this category. Alternative approaches are also envisioned that would utilize a sliding gate as opposed to a revolving one much like that of a jail cell or pocket door, again the function would largely be the same, with the sliding gate sliding to a first position to receive a fixation rod in the clamp, and sliding to a second position to prevent removal.

Figure 14:
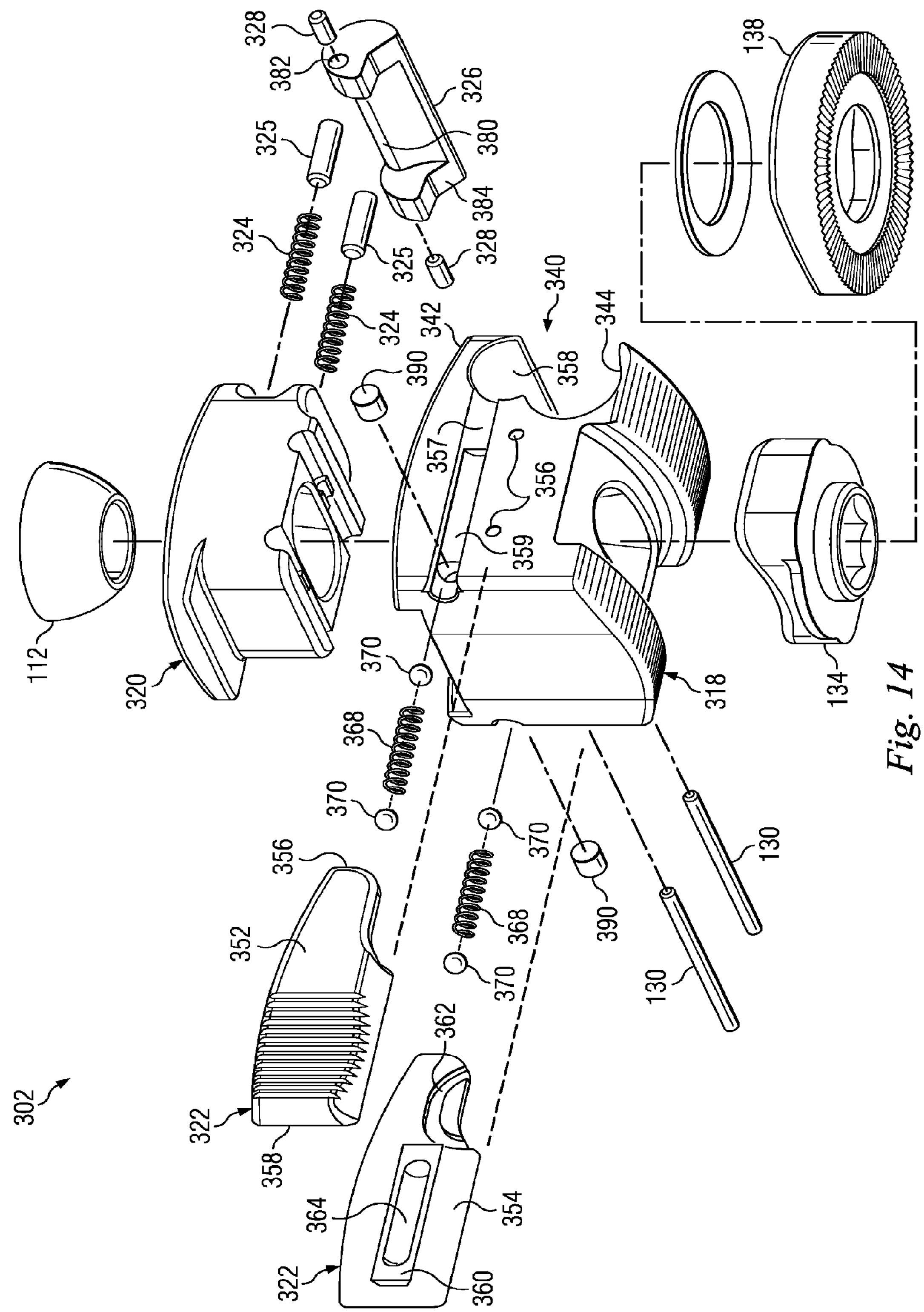
FIGS. 14 and 15 are illustrations of a clamp of the clamping assembly of FIG. 13 in exploded configurations according to one exemplary aspect of the present disclosure.
Figure 15:
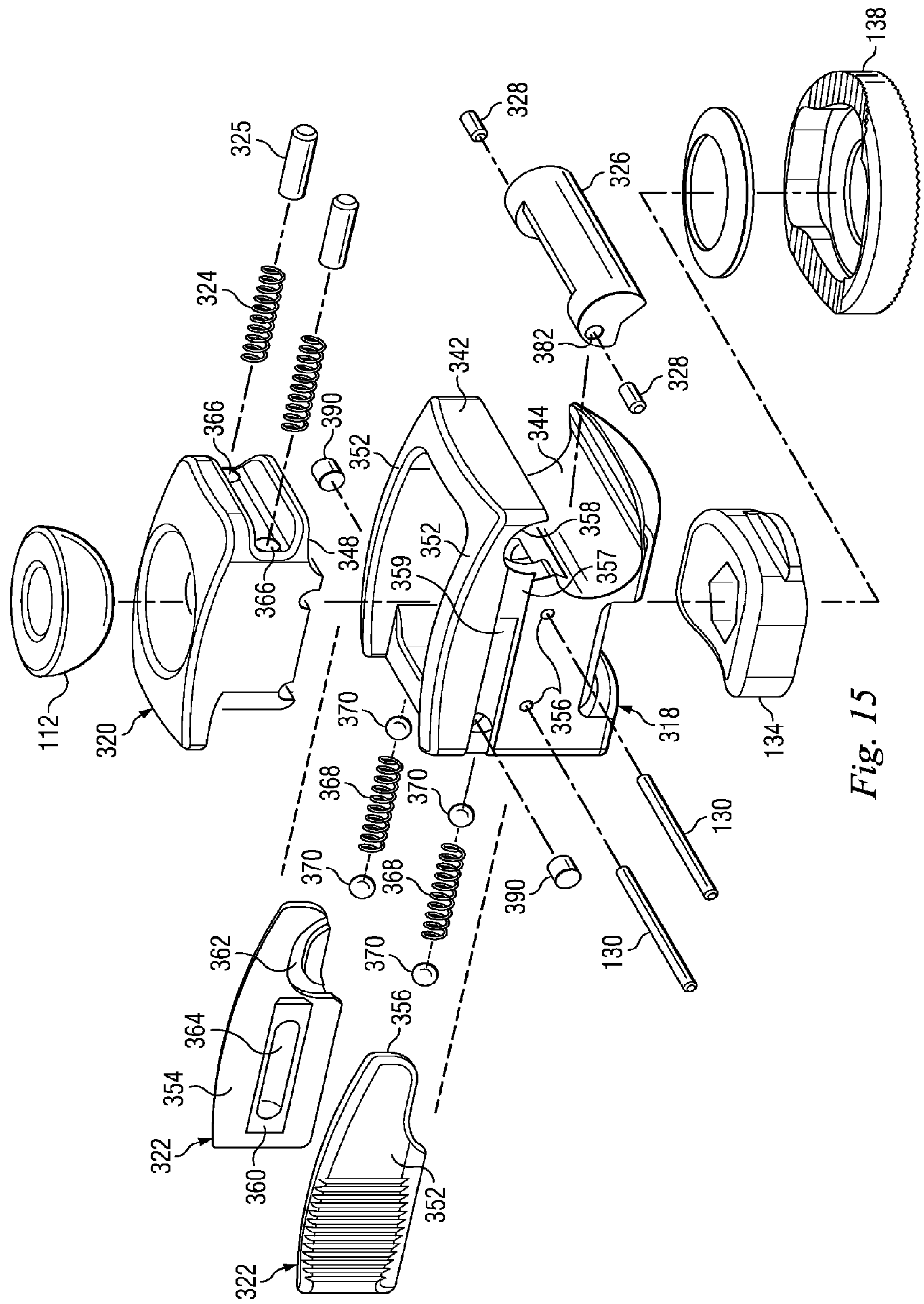
Figure 16A:
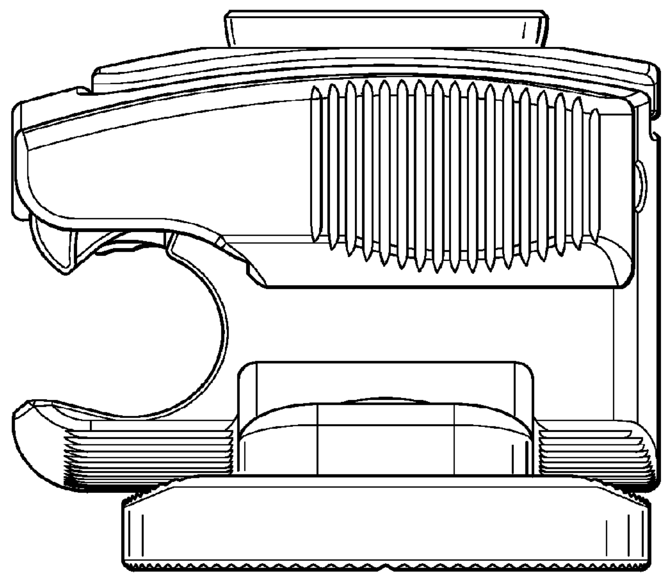
FIGS. 16A-16B are illustrations of the clamp of FIGS. 14 and 15 showing a side view and a back view respectively.
Figure 16B:
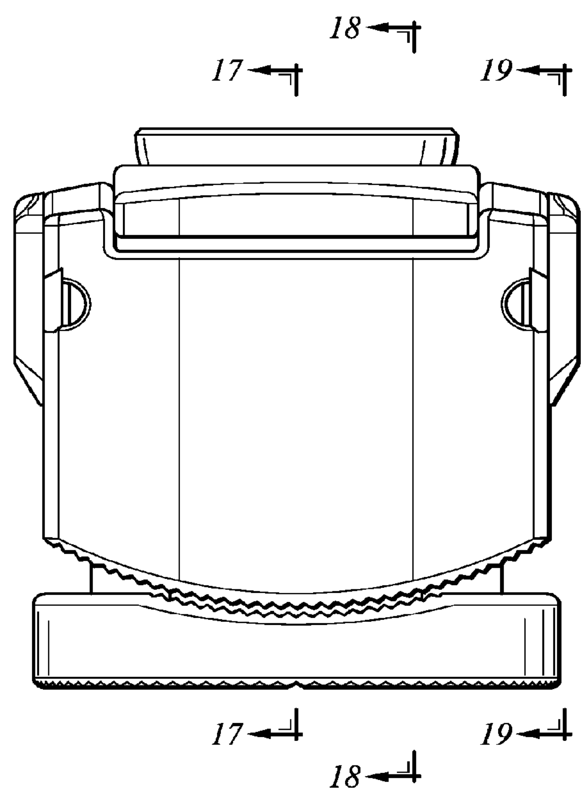
Figure 17:
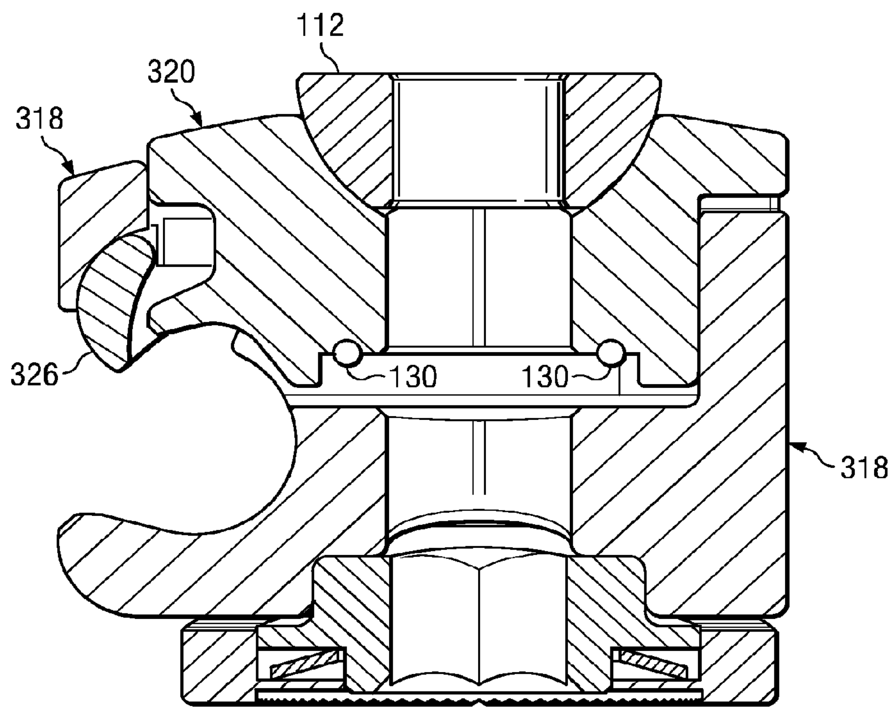
FIG. 17 is an illustration of a cross-section of the clamp of FIG. 16B taken through the lines 17-17 in FIG. 16B according to one exemplary aspect of the present disclosure.
Figure 18:
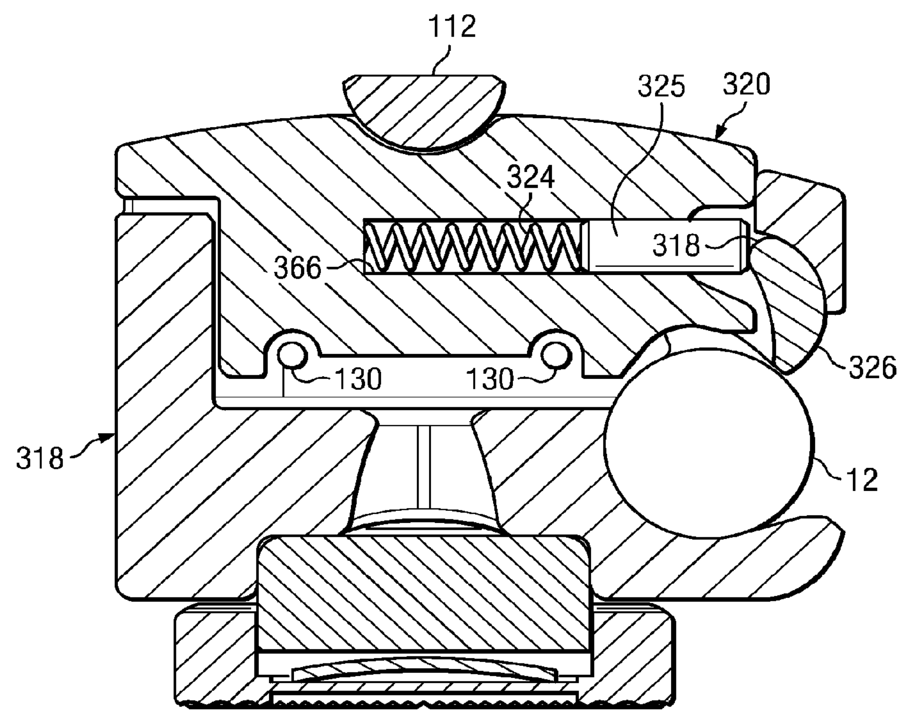
FIG. 18 is an illustration of a cross-section of the clamp of FIG. 16B taken through the lines 18-18 in FIG. 16B according to one exemplary aspect of the present disclosure.
Figure 19:
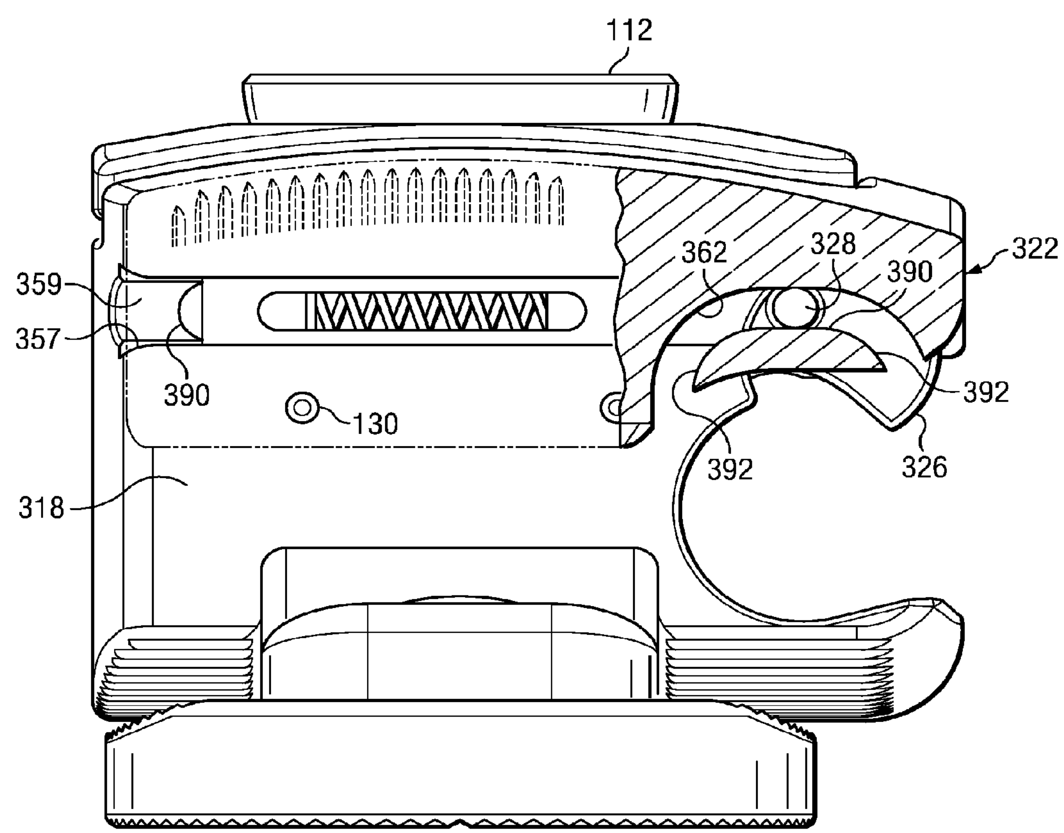
FIG. 19 is an illustration of a cross-section of the clamp of FIG. 19B taken through the lines 19-19 in FIG. 19B according to one exemplary aspect of the present disclosure.

Referring to the partial cross-section view in FIG. 19 and the exploded views of FIGS. 14 and 15, the dovetail portions 360 of the sliders 322 are engaged and allowed to slide along dovetail groove 357 of the inner jaw 318. Milled within the dovetail groove 318 is a partial biasing groove or slot 359 which in conjunction with stop pins 390 in bores in the inner jaw 318 provides bearing and capture for spring 368 against the ball or balls 370. The length of the biasing groove or slot 359 controls the installed height of the spring 368 and thus the preload generated.

The biasing groove 364 in the slider 322 is complementary to the biasing groove or slot 359 and also milled into the dovetail portion 360. Together with the biasing groove or slot 359, this provides a force that acts to bias the sliders 322 into a center position along dovetail groove 357. This force provides resistance to both forward and reverse motion of the sliders 322 relative to the inner jaw 318.

The pin groove 362 in the sliders 322 is designed to accept the gate pin 328. The contour of the pin groove 362 is configured as to control the position of the gate pin 328 as a function of the linear position of the slider 322. Here, the pin groove includes a flat portion 390 and curved portions 392. The gate pin 328 is off-center or eccentric with respect to the revolving gate 326 and effects a rotation of the revolving gate 326 if the position of the gate pin 328 is changed, since the position of the gate pin 328 is controlled by the pin groove 362 whose contour varies along the length of the sliders 322, linear motion of the sliders 322 will effect a rotation of the revolving gate 326. As such, as the sliders 322 displace relative to the gate 326, the pin groove 362 formed in the sliders 322 acts on the gate pin 328 to force it to rotate and receive or permit removal of a fixation element.

It is desirable to have the relationship between the pin groove 362 and gate pin 328 be such that when the sliders 322 are at certain positions, the gate pin 328 is prevented from rotation. This occurs where an incremental change in the position of the sliders 322 results in no motion being imparted to the gate pin 328. In effect this would represent an infinite mechanical advantage on the part of the sliders 322 over the gate pins 328. This occurs within the flat portion 390 of the pin groove 362. Beyond the flat portion 390 of the pin groove 362 on either side are the two curved sections 392. When the sliders 322 are positioned so as to have the gate pins 128 in either of these sections, motion of revolving gate 326 becomes a function of the slider position. The nature of the transition between the flat section 390 and the curved sections 392 as well as the slope of the flat section 390 and curvature of the curved sections 392 is to be tailored to provide a specific behavior. It is anticipated that many such combinations and dimensions could be utilized to provide a variety of desired results. In this embodiment, pushing the sliders 322 either forward or backward relative to the inner jaw 318 will result in the opening of the revolving door to accept the fixation element 12.

The sequence of insertion and removal of the fixation element 12 is described with reference to FIGS. 20A-20F. The insertion procedure is described with reference to FIGS. 20A-20C and the removal procedure is described with reference to FIGS. 20D-20F. FIGS. 20A-20F are partial cross-sectional views taken through the lines 19-19 in FIG. 16B. The clamp 302 of the clamping assembly 300 may be held by applying pressure across the sliders 322 with, for example, the thumb and forefinger. In this condition, referred to as the starting condition, the gate 326 partially projects into the pathway of the fixation element. The leading edge of the relief cut 384 in the gate 326 and the inner jaw 318 are particularly sized and shaped so that the distance between the leading edge of the relief cut 384 and the inner jaw 318 is less than the diameter of the fixation element 12. As a fixation element 12 is pressed into the opening in the clamp 302, it comes into contact with the leading edge of the relief cut 384 in the revolving gate 326. This pressure, along with the forces on the sliders 322 forces the revolving gate 326 to rotate about its axis in opposition to the biasing element spring 324.

Figure 20A:
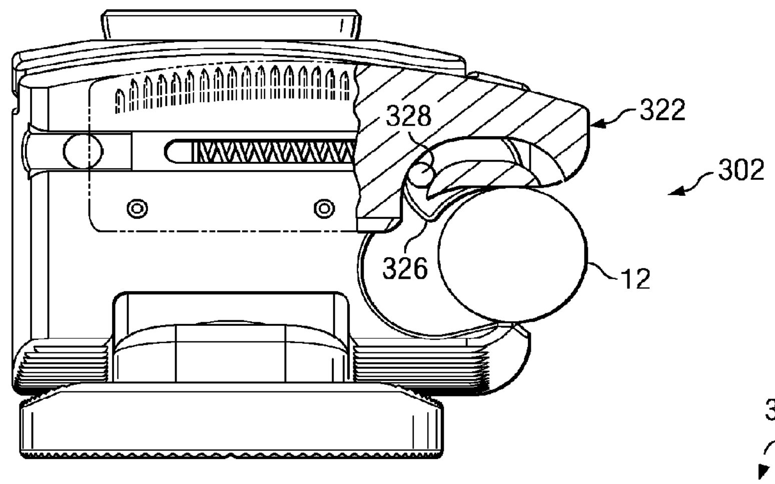
FIGS. 20A-20F are series of illustrations of the clamp of FIGS. 14 and 15 with a fixation element being introduced into the clamp and being removed from the clamp.

As can be seen in FIG. 20A, the slider 322 is moved toward the clamping side in the direction of the opening 340. Accordingly, when the clamp 302 contacts the fixation element 12, additional movement by the surgeon results in the jaws 318, 320 abutting the fixation element 12 and the sliders 322 moving relative to the jaws 318, 320 to the forward position shown in FIG. 20A. Thus, the sliders 322 can be pushed forward merely by gripping the sliders and pushing the clamp 302 toward the fixation element 12.

Figure 20B:
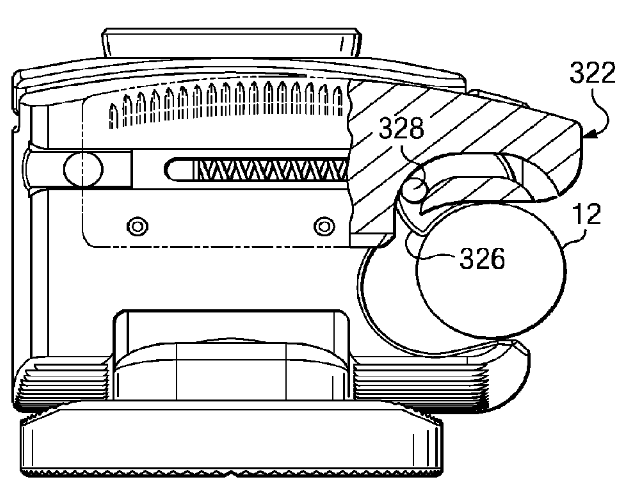

FIG. 20B shows the relief cut 384 in place adjacent the fixation element 12 and about to be rotated due to forces applied by the fixation element 12. Continued displacement of the fixation element 12 into the opening 340 in the clamp 302 eventually rotates the gate 326 to permit the fixation element 12 to pass and enter the opening. During this time, the gate 326 continues to rotate until the fixation element 12 passes through the opening. This condition is referred to herein as the open condition, where the gate 326 is in the transition region permitting the fixation element 12 to pass into the clamp 302. Accordingly, in this open condition, the distance between the leading end of the relief cut 384 and the inner jaw 318 is equal to or greater than the diameter of the fixation element 12. Eventually, when the fixation element 12 is advanced into the clamp 302 deeply enough to provide clearance, the trailing end of the gate relief cut 384 acts on the fixation element 12 to hold it in place. Accordingly, the trailing end of the gate relief cut 384 physically or mechanically interferes with the fixation element 12 in a manner preventing removal of the fixation element from the clamp 302. Here, the clamp 302 is in a provisionally locked condition.

Figure 20C:
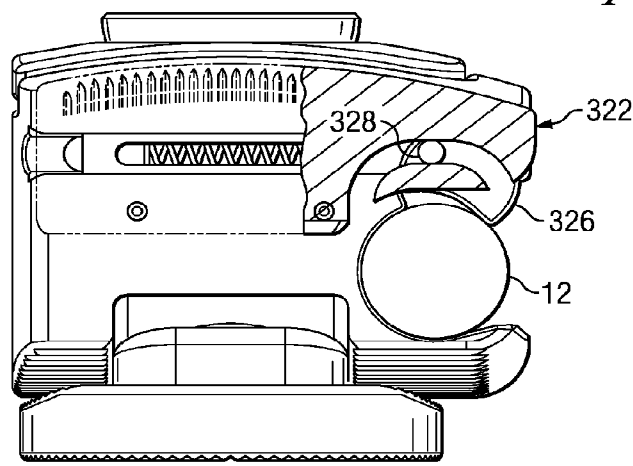

FIG. 20C shows the fixation element 12 seated in the slot forming the fixation element contacting surface 144 and the revolving gate 326 is shown in its locked position. Forces acting on the fixation element 12 to unseat it are now opposed by the fact that the gate pin 328 is in the flat portion 390 in the pin groove 362 which means it is not back drivable and as such the fixation element 12 remains retained. This operates properly because the rotational force is attempting to move the gate pin 328 in a direction transverse to the direction of the pin groove 362. That is, the rotational force is attempting to move the gate pin 328 into the groove wall or edges. The groove walls or edges mechanically prevent movement in this transverse direction.

With the fixation element 12 disposed as shown in FIG. 20C, the fixation element is physically blocked or secured within the clamp 302 in the provisionally locked condition. This provisional condition allows a surgeon to snap or press the clamp assembly onto a fixation element, but still manipulate or adjust the clamp position relative to the fixation element.

Figure 20D:
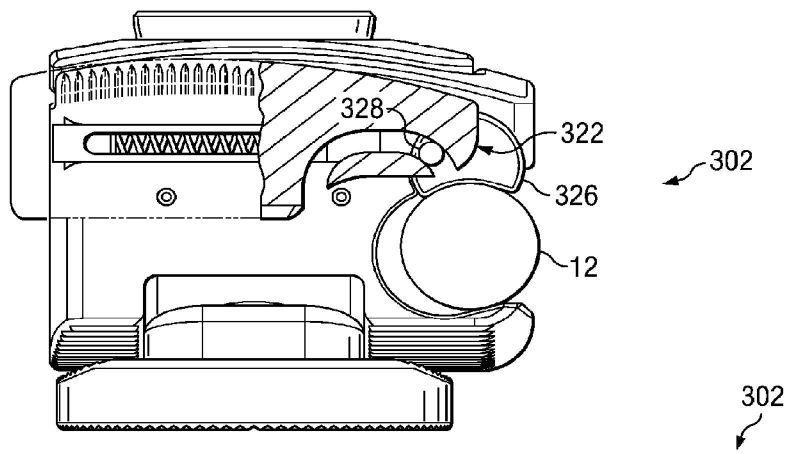
Figure 20E:
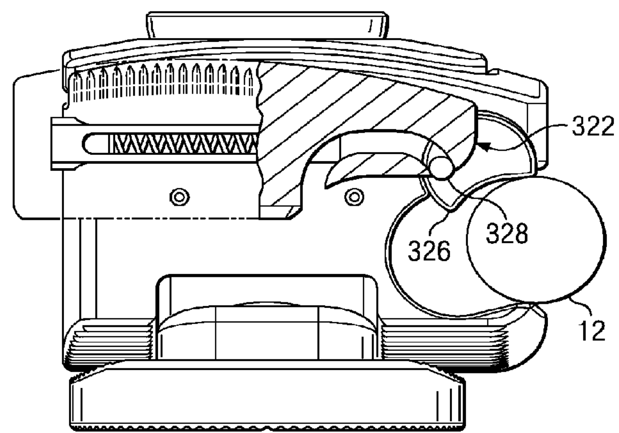
Figure 20F:
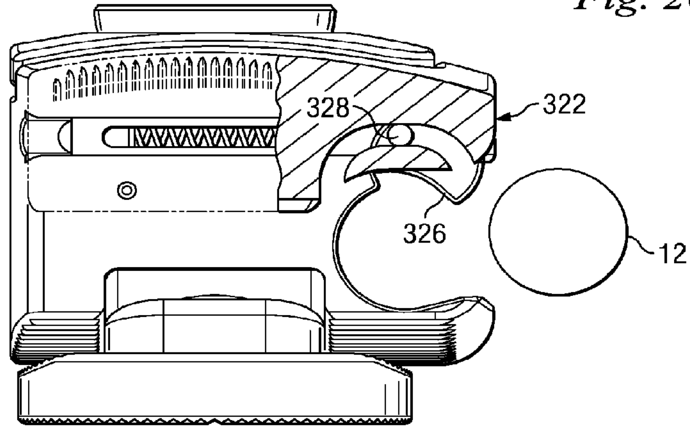

The removal structure and operation will now be described. Sliding the sliders 322 toward the rearward side of the clamp 302 within the dovetail groove 357 of the inner jaw 318 displaces the pin groove 362 relative to the gate pin 328 as shown in FIG. 20D. Accordingly, the trailing edge of the milled pin groove 362 comes into contact with the revolving gate pin 328. This pressure forces a clockwise rotation of the revolving gate 326 such that the relief cut 384 is rotated into an orientation that allows passage of the fixation element 12. FIG. 20E shows the fixation element 12 partially out of the jaw recess, and FIG. 20C shows the fixation element completely clear of the jaw recess, and the slider returned to its centered or neutral state under the force of the spring 368.

The process of applying a clamping load or transitioning the clamp 302 from the provisional locked condition to the fully locked or final locked condition is the same as that described above and will not be repeated here.

Like the clamp 102, the clamp 302 secures a fixation element at least in a provisionally locked condition without actual displacement of the upper jaw 320 relative to the inner jaw 318. As is apparent from the discussion above, the gate 326 adjusts in a manner relative to one of the lower and upper jaws to change the size of the fixation element-receiving opening, without requiring relative displacement of the upper and inner jaws. In the embodiment shown, only when the clamp condition is changed from the provisional lock to the final lock do the upper and inner jaws move relative to one another.

The embodiments shown employ revolving or rotating gates. As indicated above, flappers, check valves, draw bridges, and swinging or hinged doors all fall within this category of rotating gates. Alternative approaches are also envisioned that would utilize a sliding gate, much like that of a jail cell or pocket door, again the function would largely be the same, with the sliding gate sliding to a first position to receive a fixation rod in the clamp, and sliding to a second position to prevent removal. These types of sliding gates may be considered to revolve about a center of rotation spaced apart from the gate itself. For example in some embodiments, the gate is disposed to revolve about a center of rotation spaced in the clamping assembly at a location not directly adjacent the jaws, such that the gate moves along an arc defined by a larger radius than that of the embodiment shown. In some examples, the gate moves along an arc defined by a center of rotation off of or outside the clamping assembly. In yet other embodiments, the gate moves along an arc defined by a center of rotation located an infinite distance from the gate. Accordingly, the gate moves in a substantially linear direction.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A clamp assembly configured to secure a fixation element of an external fixation assembly, comprising:
- a first jaw;
- a second jaw disposed relative to the first jaw, the first and second jaws cooperatively positioned to receive the fixation element; and
- a revolving gate moveable between an open condition and a provisionally locked condition, wherein:
  - in the open condition, the gate and the first jaw form a first sized opening that allows the fixation element to be removed from and introduced between the first and second jaws; and
  - in the provisionally locked condition, the gate and the first jaw form a second sized opening that prevents removal of the fixation element from between the first and second jaws, but allows the fixation element to slide and rotate relative to the first and second jaws,
- wherein the gate has a substantially cylindrical configuration with a relief formed therein, the relief being disposed in a manner that when the gate is in the open condition, the relief allows the fixation element to be removed from and introduced between the first and second jaws.

2. The clamp assembly of claim 1, further comprising a biasing element that is positioned and configured to bias the gate toward the provisionally locked condition.

3. The clamp assembly of claim 1, further comprising a release mechanism configured to displace the gate to the open condition allowing the fixation element to be removed from and introduced between the first and second jaws.

4. The clamp assembly of claim 3, wherein the release mechanism comprises a slider actuatable by a user and a gate release portion associated with the slider, wherein the slider and gate release portion are configured such that actuation of the slider manually displaces the gate release portion.

5. The clamp assembly of claim 4, wherein the slider is moveable between a neutral position, a forward position, and a rearward position, the neutral position of the slider corresponding to the provisionally locked condition of the gate.

6. The clamp assembly of claim 5, wherein movement of the slider into the forward position moves the gate to the open condition and movement of the slider into the rearward position causes the gate to expel the fixation element from the clamp.

7. The clamp assembly of claim 1, wherein the gate is moveable to the provisionally locked condition to prevent removal of the fixation element from between the first and second jaws without any relative movement of the first and second jaws.

8. A clamp assembly configured to secure a fixation element of an external fixation assembly, comprising:
- a first jaw;
- a second jaw disposed relative to the first jaw, the first and second jaws cooperatively positioned to receive the fixation element; and
- a revolving gate moveable between an open condition and a provisionally locked condition, wherein:

in the open condition, the gate and the first jaw form a first sized opening that allows the fixation element to be removed from and introduced between the first and second jaws; and in the provisionally locked condition, the gate and the first jaw form a second sized opening that prevents removal of the fixation element from between the first and second jaws, but allows the fixation element to slide and rotate relative to the first and second jaws, wherein the gate has a substantially cylindrical configuration with a ramp formed therein, and movement of the gate from the open condition to the provisionally locked condition causes a progressive lessening of the distance between the ramp and a fixation element receiving slot in the first jaw.

9. The clamp assembly of claim 8, further comprising a biasing element that is positioned and configured to bias the gate toward the provisionally locked condition.

10. The clamp assembly of claim 8, further comprising a release mechanism configured to displace the gate to the open condition allowing the fixation element to be removed from and introduced between the first and second jaws.

11. The clamp assembly of claim 10, wherein the release mechanism comprises a slider actuatable by a user and a gate release portion associated with the slider, wherein the slider and gate release portion are configured such that actuation of the slider manually displaces the gate release portion.

12. The clamp assembly of claim 11, wherein the slider is moveable between a neutral position, a forward position, and a rearward position, the neutral position of the slider corresponding to the provisionally locked condition of the gate.

13. The clamp assembly of claim 12, wherein movement of the slider into the forward position moves the gate to the open condition and movement of the slider into the rearward position causes the gate to expel the fixation element from the clamp.

14. The clamp assembly of claim 8, wherein the gate is moveable to the provisionally locked condition to prevent removal of the fixation element from between the first and second jaws without any relative movement of the first and second jaws.

15. A clamp assembly configured to secure a fixation element of an external fixation assembly, comprising:

a first jaw;

a second jaw disposed relative to the first jaw, the first and second jaws cooperatively positioned to receive the fixation element;

a revolving gate moveable between an open condition and a provisionally locked condition, wherein:

in the open condition, the gate and the first jaw form a first sized opening that allows the fixation element to be removed from and introduced between the first and second jaws; and in the provisionally locked condition, the gate and the first jaw form a second sized opening that prevents removal of the fixation element from between the first and second jaws, but allows the fixation element to slide and rotate relative to the first and second jaws; and a lock configured to be actuated to prevent the fixation element from sliding and rotating relative to the first and second jaws, wherein the lock comprises:

a post component disposed through respective holes in the first and second jaws; and a nut threadably engaging the post component and configured to be tightened to cause the first and second jaws to move relative to one another to prevent the fixation element from sliding and rotating relative to the first and second jaws.

16. The clamp assembly of claim 15, further comprising a biasing element that is positioned and configured to bias the gate toward the provisionally locked condition.

17. The clamp assembly of claim 15, further comprising a release mechanism configured to displace the gate to the open condition allowing the fixation element to be removed from and introduced between the first and second jaws.

18. The clamp assembly of claim 17, wherein the release mechanism comprises a slider actuatable by a user and a gate release portion associated with the slider, wherein the slider and gate release portion are configured such that actuation of the slider manually displaces the gate release portion.

19. The clamp assembly of claim 18, wherein the slider is moveable between a neutral position, a forward position, and a rearward position, the neutral position of the slider corresponding to the provisionally locked condition of the gate.

20. The clamp assembly of claim 19, wherein movement of the slider into the forward position moves the gate to the open condition and movement of the slider into the rearward position causes the gate to expel the fixation element from the clamp.

21. The clamp assembly of claim 15, wherein the gate is moveable to the provisionally locked condition to prevent removal of the fixation element from between the first and second jaws without any relative movement of the first and second jaws.

* * * * *